United States Patent [19]

Stein et al.

[11] Patent Number: 4,977,174

[45] Date of Patent: Dec. 11, 1990

[54] 7-OXABICYCLOHEPTANE IMIDAZOLE PROSTAGLANDIN ANALOGS USEFUL IN THE TREATMENT OF THROMBOTIC AND VASOSPASTIC DISEASE

[75] Inventors: Philip D. Stein, Princeton; Steven E. Hall, Ewing Township, both of N.J.

[73] Assignee: E. R. Squibb & Sons, Inc., Princeton, N.J.

[21] Appl. No.: 492,504

[22] Filed: Mar. 12, 1990

Related U.S. Application Data

[63] Continuation-in-part of Ser. No. 364,408, Jun. 12, 1989.

[51] Int. Cl.$^5$ .................. C07D 405/06; C07D 257/04; A61K 31/41; A61K 31/415
[52] U.S. Cl. ..................... 514/382; 514/397; 548/250; 548/251; 548/336
[58] Field of Search ........... 548/250, 251, 336; 514/397, 382

[56] References Cited

U.S. PATENT DOCUMENTS

| | | | |
|---|---|---|---|
| 4,416,896 | 11/1983 | Nakane et al. | 424/285 |
| 4,418,076 | 11/1983 | Nakane et al. | 424/285 |
| 4,463,015 | 7/1984 | Haslanger et al. | 424/285 |
| 4,474,804 | 10/1984 | Das et al. | 424/285 |
| 4,489,089 | 12/1984 | Wright et al. | 548/336 |
| 4,500,540 | 2/1985 | Hamilton et al. | 514/397 |
| 4,522,949 | 6/1985 | Das et al. | 514/469 |
| 4,536,513 | 8/1985 | Das et al. | 514/469 |
| 4,663,336 | 5/1987 | Nakane et al. | 514/381 |
| 4,663,337 | 5/1987 | Das et al. | 514/382 |

FOREIGN PATENT DOCUMENTS

| | | | |
|---|---|---|---|
| 62000470A | 6/1985 | Japan | 548/341 |
| 2126218 | 3/1984 | United Kingdom | 548/341 |

OTHER PUBLICATIONS

As Belo Bioorg Chem, 04.03.81-SU278256 (23.22.87).
Chem. Abs. CA Selects: Prostaglandins Issue 12, 1988 108:198903m, Kuz'mitskii, B. B. et al.

CA Selects: Prostaglandins, Issue 12, 1988, 108:204363d, Lakhvich, F. A. et al.

*Primary Examiner*—Alan L. Rotman
*Assistant Examiner*—Joseph K. McKane
*Attorney, Agent, or Firm*—Burton Rodney

[57] ABSTRACT

7-Oxabicycloheptane imidazole prostaglandin analogs are provided which are useful in treating thrombotic and vasospastic disease and have the structural formula

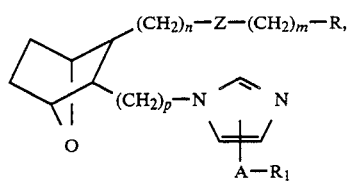

wherein m is 0, 1, 2, 3 or 4; n is 1, 2 or 3; and p is 1, 2 or 3; Z is —CH=CH—, —CH$_2$CH$_2$— or

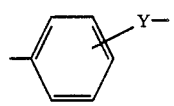

wherein Y is 1 or a single bond; R is CO$_2$H, CO$_2$lower alkyl, CO$_2$alkali metal, CONHSO$_2$R$_2$ (wherein R$_2$ is lower alkyl or aryl) or —CH$_2$-5-tetrazolyl; A is CHOH, C=O,

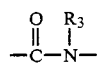

(wherein R$_3$ is H or lower alkyl), or a single bond; R$_1$ is lower alkyl, aryl, cycloalkyl or H, R$_1$ can be H only when A is a single bond.

31 Claims, No Drawings

7-OXABICYCLOHEPTANE IMIDAZOLE PROSTAGLANDIN ANALOGS USEFUL IN THE TREATMENT OF THROMBOTIC AND VASOSPASTIC DISEASE

REFERENCE TO RELATED APPLICATIONS

This application is a continuation-in-part of application Ser. No. 364,408 filed June 12, 1989.

DESCRIPTION OF THE INVENTION

The present invention relates to 7-oxabicycloheptane imidazole prostaglandin analogs which are thromboxane $A_2$ (TXA$_2$) receptor antagonists or combined thromboxane $A_2$ receptor antagonists/thromboxane synthatase inhibitors useful, for example, in the treatment of thrombotic and/or vasospastic disease and have good duration of action. These compounds have the structural formula I

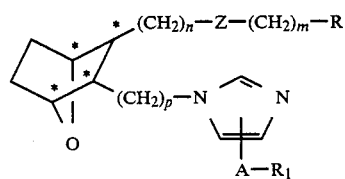
I and including all stereoisomers thereof, wherein
m is 0, 1, 2, 3 or 4; n is 1, 2, or 3; and p is 1, 2 or 3;
Z is —CH=CH—, —CH$_2$CH$_2$— or

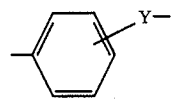

(wherein Y is O or a singe bond); Y—with the provisos that when Z is

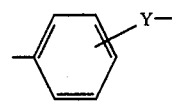

and m is 0, then Y is a single bond; and when Z is —CH=CH— or —CH$_2$CH$_2$—, m is 1, 2, 3 or 4;
R is CO$_2$H, CO$_2$lower alkyl, CO$_2$alkali metal CONHSO$_2$R$_2$ (wherein R$_2$ is lower alkyl or aryl) or —CH$_2$-5-tetrazolyl;
A is CHOH,

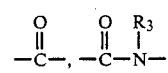

(wherein R$_3$ is H or lower alkyl), or a single bond; and
R$_1$ is H, lower alkyl, aryl, or cycloalkyl; R$_1$ may be H only when A is a single bond.

Thus, the compounds of the invention encompass the following types of compounds:

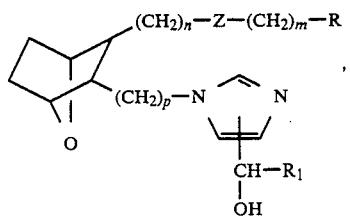
IA

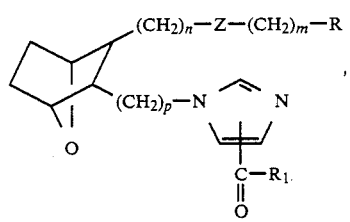
IB

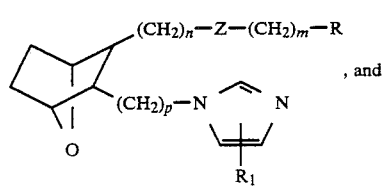
IC
, and

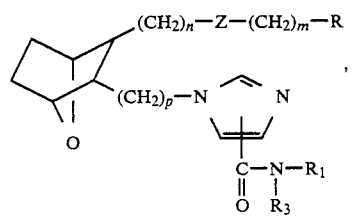
ID

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups and/or 1 or 2 hydroxy groups.

The term "aryl" or "Ar" as employed herein refers to monocyclic or bicyclic aromatic groups containing from 6 to 10 carbons in the ring portion, such as phenyl, naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br or F), lower alkoxy, aryloxy, alkylthio, alkylsulfinyl, alkylsulfonyl, arylthio, arylsulfinyl and/or arylsulfonyl.

The term "aralkyl", "aryl-alkyl" or "aryllower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

Preferred are those compounds of formula I wherein m is 2, n is 1, p is 1, R is $CO_2H$, A is CHOH, C=O, a single bond,

and $R_1$ is cycloalkylalkyl, or H, and —A—$R_1$ is in the 4-position of the imidazole ring, Z is —CH=CH— or

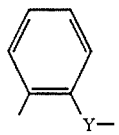

and Y is a single bond.

The various compounds of the invention may be prepared as outlined below.

The compounds of formula I of the invention may be prepared as follows.

Compounds of the invention where A is CHOH are prepared starting with imidazole alcohol hydrochloride A

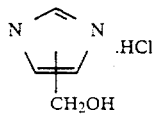

which is neutralized by passing A through a column of anion exchange resin, hydroxy form, to form the free base B

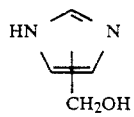

The free base B is then oxidized by treating a solution of B in an inert organic solvent such as dioxane, benzene or methylene chloride with manganese dioxide, or barium manganate under an inert atmosphere such as argon, to form the aldehyde C

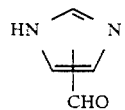

Aldehyde C is then made to undergo a Grignard reaction by teating C with a Grignard reagent of the structure

(prepared by adding bromide E

in an appropriate inert organic solvent such as tetrahydrofuran or diethyl ether to a stirred suspension of Mg turnings in an inert organic solvent such as tetrahydrofuran, or diethyl ether), employing a molar ratio of E : C of within the range of from about 1.5:1 to about 5:1, to form the alcohol F

The alcohol F is treated with a protecting compound such as chlorodimethyl-t-butylsilane in the presence of an amine base such as triethylamine and an inert organic solvent such as dimethyl formamide or methylene chloride, employing conventional procedures, to form the protected compound G

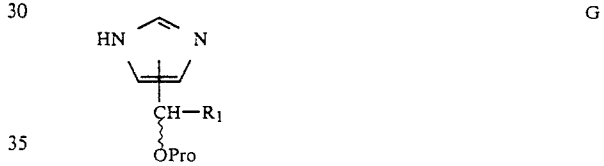

wherein Pro represents a protecting group.

Examples of protecting compounds suitable for use herein in reacting with alcohol F include but are not limited to

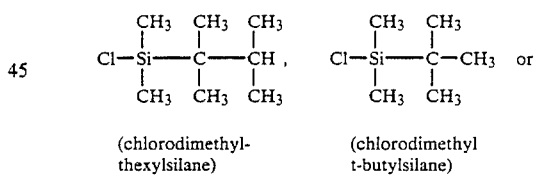

(chlorodimethyl-thexylsilane)   (chlorodimethyl t-butylsilane)

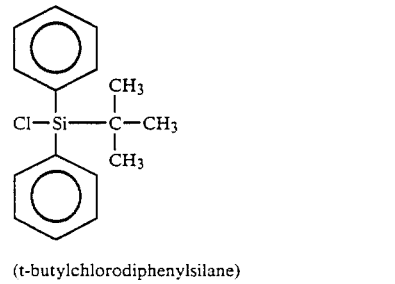

(t-butylchlorodiphenylsilane)

A solution of the protected alcohol G is formed in an inert solvent such as dimethylsulfoxide which is treated with a base such as sodium hydride (optionally in the presence of an inert carrier such as mineral oil) or lithium diisopropylamide (in tetrahydrofuran or hexanes). The resulting solution is treated with tosylate H

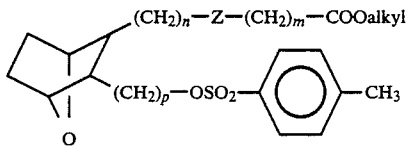

employing a molar ratio of H : G of within the range of from about 1:1 to about 0.2:1 to form imidazole compound II

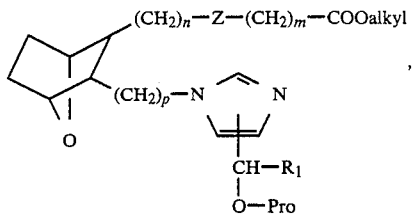

Compound II is then deprotected using standard procedures, for example by treating a solution of II in an alcohol solvent, such as methanol, under an inert atmosphere, such as argon, with acetyl chloride to form the corresponding alcohol IE

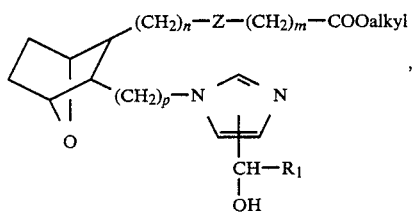

Compounds of the invention wherein A is C=O may be prepared by subjecting alcohol ester IE to allylic oxidation by treating a solution of IE in dioxane or benzene with an oxidizing agent such as activated manganese dioxide under an inert atmosphere such as argon, at a temperature within the range of from about 20° C. to about 125° C., to form ester of the invention IF

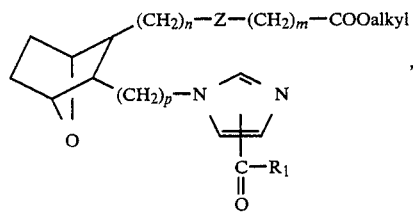

In a preferred embodiment, compounds of the invention wherein A is C=O may be prepared by treating tosylate H with imidazole J

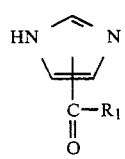

in the presence of a solvent such as dimethylformamide, THF or preferably dimethylsulfoxide, and base such as sodium hydride, potassium hydride, potassium tert-butoxide or 1,4-diazabicyclo[2.2.1]octane (DABCO), at a temperature within the range of from about 25° to about 90° C., employing a molar ratio of H:J of within the range of from about 0.95:1 to about 0.4:1, to form imidazole compound IF.

Compounds of the invention wherein A is a single bond and $R_1$ is other than H may be prepared by heating a solution of imidazole K

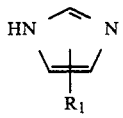

and tosylate H in anhydrous inert organic solvent such as anhydrous dimethylformamide, dimethyl sulfoxide or hexamethylphosphorictriamide (HMPA), at a temperature within the range of from about 20° C. to about 125° C., employing a molar ratio of K : H of within the range of from about 1:1 to about 5 1, to form ester of the invention IG

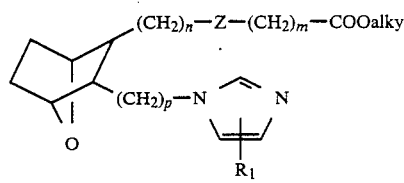

Compounds of the invention wherein A is a single bond and $R_1$ is H may be prepared by heating a solution of tosylate H and imidazole

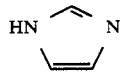

in an inert organic solvent such as dimethylformamide, dimethyl sulfoxide or HMPA, under an inert atmosphere such as argon, at a temperature within the range of from about 20° C. to about 125° C., employing a molar ratio of H:imidazole of within the range of from about 1.1:1 to about 0.17:1, to form the ester of the invention IH

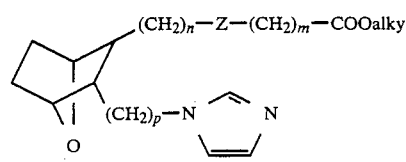

Compounds of the invention wherein A is

may be prepared by starting with imidazole carboxylic acid L

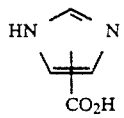

which is treated first with a carboxyl activating agent such as 1,1′-carbonyl diimidazole in an inert organic solvent such as dimethylformamide and subsequently with an amine salt of the formula M

in the presence of a tertiary amine base such as triethylamine to form the amide N

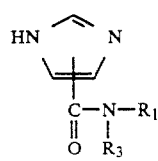

Amide N is then condensed with tosylate H, employing a molar ratio of H:N of within the range of from about 1:1 to about 0.2:1, in the presence of base such as NaH, lithium diisopropyl amide or potassium t-butoxide, and an inert solvent such as dimethyl sulfoxide, dimethyl formamide or HMPA, at a temperature within the range of from about 20° C. to about 125° C., to form compound IJ

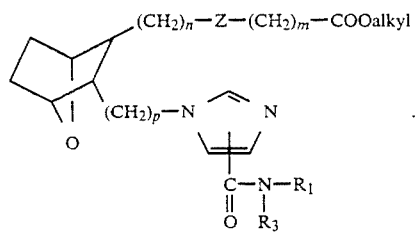

The esters IE, IF, IG, IH and IJ may be converted to the corresponding acids, that is IK

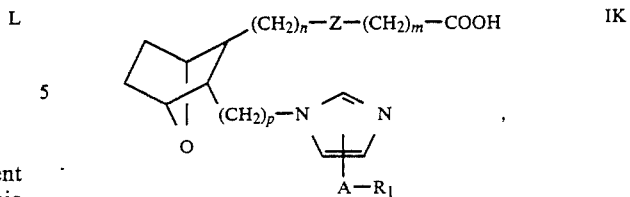

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention.

Compounds of the invention wherein R is CONHSO$_2$R$_2$, that is IL

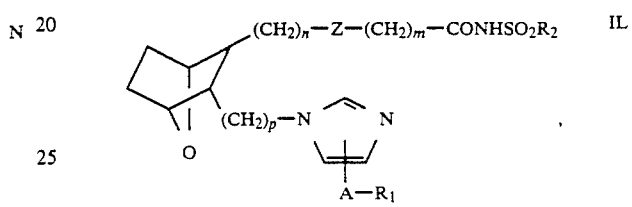

are prepared by treating acid IK with a sulfonamide of the structure P

in the presence of a coupling agent such as carbonyldiimidazole or ethyl -3(3-dimethylamino)propylcarbodiimide (WSC) and 4-dimethylaminopyridine, under an inert atmosphere such as argon, employing a molar ratio of P:IK of within the range of from about 0.8:1 to about 1.2:1, to form sulfonamide IL.

Compounds of the invention wherein R is —CH$_2$—5-tetrazolyl and Z is —CH=CH—, that is IM

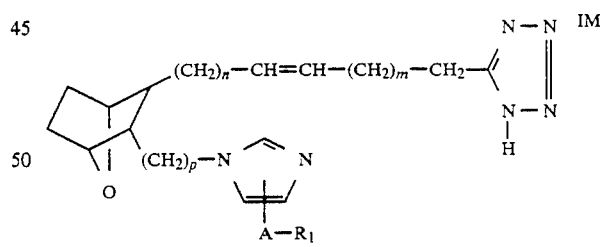

are prepared using the methodology set out above except substituting H′ for H to form protected tetrazole IN

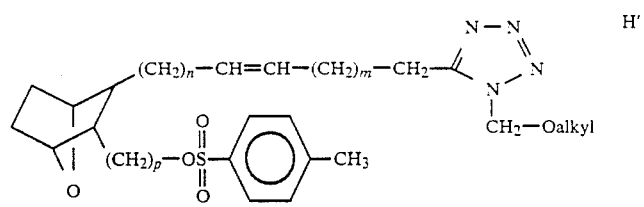

-continued

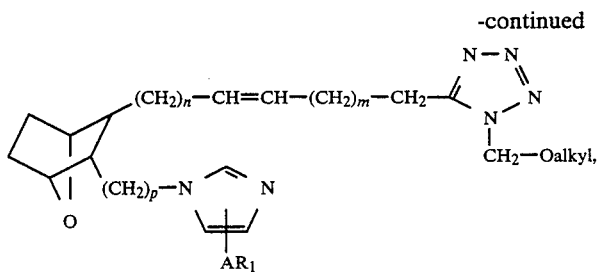        IN which is deprotected using methodology familiar to those skilled in the art to form IM. The starting tosylate H′ is prepared from alcohol III (prepared as described in U.S. Pat. 4,663,336)

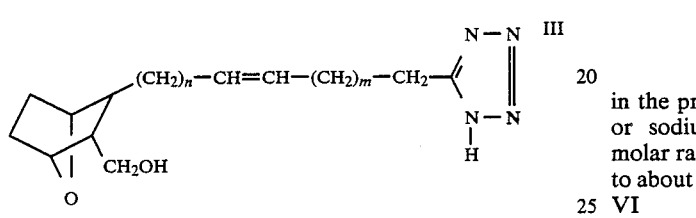        III by treatment with a protecting agent such as Hal—CH$_2$O—alkyl in the presence of a base such as K$_2$CO$_3$ or NaH to form protected tetrazole IV

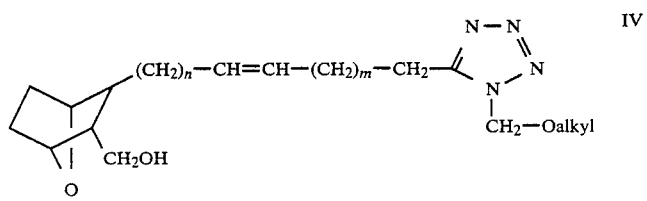        IV which is optionally homologated to alcohol V

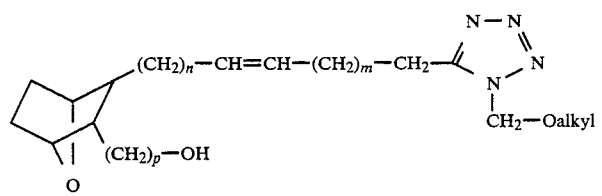        V using the procedure as described in U.S. Pat. No. 4,663,336. Alcohol V is converted to the tosylate H′ by treatment with p-toluenesulfonyl chloride in an inert solvent such as methylene chloride and an amine such as pyridine.

Compounds of the invention wherein Z is —CH═CH— and R is —CH$_2$-5-tetrazolyl, that is IM are also prepared by treating hemiacetal Q (prepared as described in U.S. Pat. No. 4,654,356)

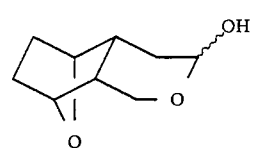        Q with a Wittig reagent of the structure R

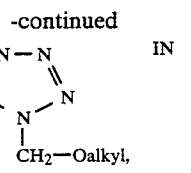        R in the presence of a base, such as potassium t-butoxide or sodium hydride-dimethyl sulfoxide employing a molar ratio of Q:R of within the range of from about 1:1 to about 0.2:1 to form the hydroxymethyl compound VI

VI

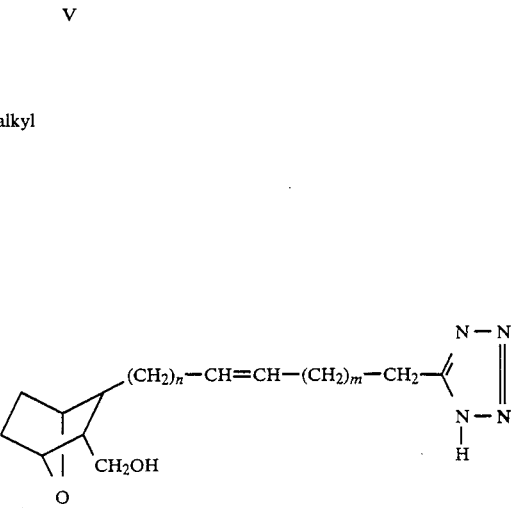

which is treated with protecting compound S

Pro-Halide        (S)

for example, bromomethyl methyl ether in the presence of base to form the protected tetrazole VII

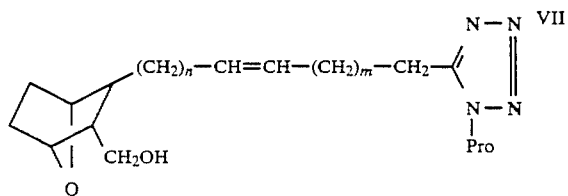

The protected tetrazole VII may then be used to form the various compounds of the formula IP

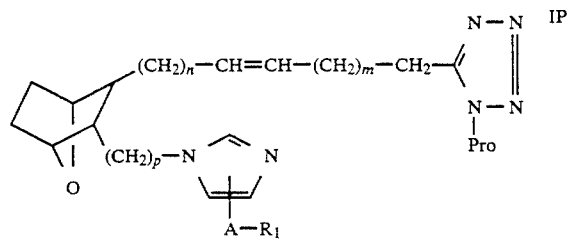

which is deprotected by treatment with aqueous acid such as aqueous hydrochloric acid to form compounds of the invention IO.

Compounds of the invention wherein R is —, CH$_2$—5—tetrazolyl, Z is

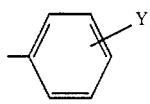

and Y is a single bond, that is IQ

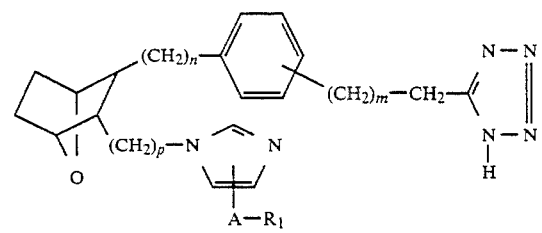

are prepared by subjecting esters IE, IF, IG, IH or IJ where Z is

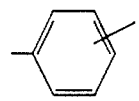

to reduction with a hydride reagent such as lithium borohydride or sodium borohydride to afford alcohol VIII

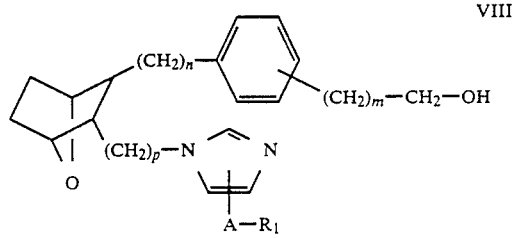

which is converted to the bromide on treatment with triphenylphosphonium dibromide in an inert solvent such as toluene. The bromide is then converted to nitrile IX on treatment with an alkali metal cyanide in a polar solvent such as methanol/water.

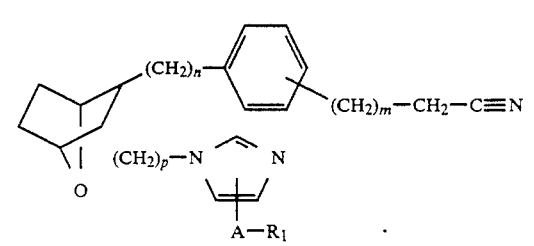

Compounds of the invention wherein R is —CH$_2$—5—tetrazolyl, Z is

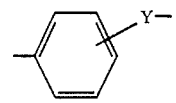

and Y=O, that is IR

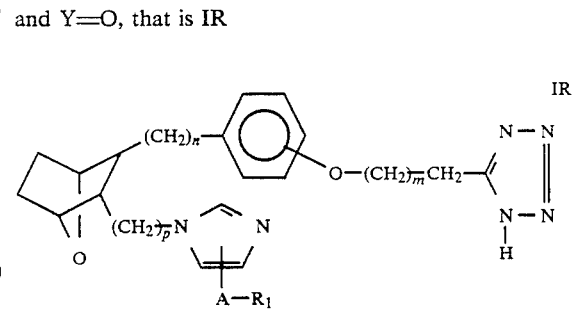

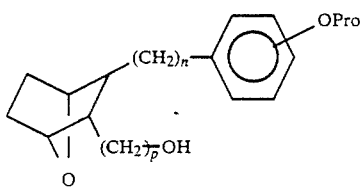

are prepared by conversion of alcohol X to XI using the procedures set out herein for conversion of alcohol ester XIX to final products. Alcohol X may be prepared from alcohol XXII employing conventional homologation techniques as described in U.S. Pat. No. 4,663,336.

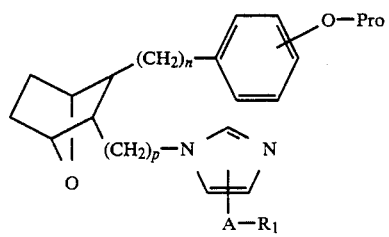  XI

XI is converted to nitrile XII

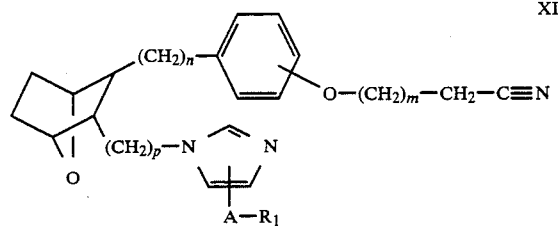  XII by deprotection, for example with aqueous HCl when Pro is methoxymethyl followed by alkylation of the resulting phenol with halonitrile T in the Hal—$(CH_2)_n$—CN     (T)

presence of a base such as sodium hydride or potassium carbonate.

The nitriles are then subjected to a cycloaddition reaction by treating IX or XII with sodium azide in the presence of ammonium chloride, dimethylformamide and lithium chloride at temperatures from about 100° C. to about 130° C. to form IQ and IR respectively.

Compounds of the invention wherein R is —$CH_2$-5-tetrazolyl, and Z is —$(CH_2)_2$—that is IS

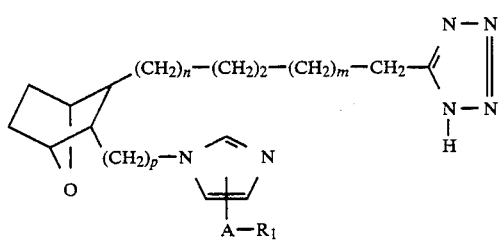  IS are prepared by subjecting ester IM to reduction with hydrogen in the presence of a catalyst such as palladium/charcoal or palladium hydroxide/carbon in the presence of an inert solvent such as ethyl acetate or acetic acid to afford IS.

Compounds of formula I wherein Z is —$(CH_2)_2$— may be prepared from acid IK where Z is —CH═CH— by subjecting IK to hydrogenation using, for example, a hydrogenation catalyst, such as palladium on charcoal, in the presence of an inert organic solvent such as ethyl acetate (EtOAc) or acetic acid (AcOH) to form acid of the invention IT

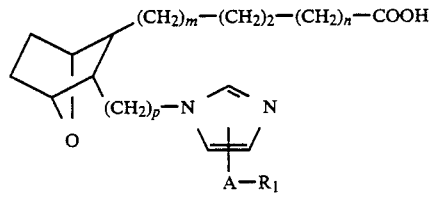  IT

Starting tosylate H where Z is

Y is a single bond and m is 1, 2, 3 or 4 are prepared starting with bromophenylalkyl alcohol U

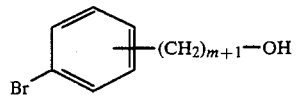  U where m is 1, 2, 3 or 4 which is treated with a protecting compound such as t-butylchlorodiphenylsilane, in the presence of an amine base such as triethylamine and an inert solvent, employing conventional procedures, to form the protected bromophenylalkyl compound V

  V wherein Pro represents a protecting group.

Examples of protecting compounds suitable for use herein are as described hereinbefore.

The protected compound V is then transmetallated by treatment with t-$C_4H_9Li$ or n-$C_4H_9Li$ in the presence of diethyl ether or tetrahydrofuran at reduced temperature of from about −100° to about 0° C. or preferably is subjected to a Grignard reaction by treatment with magnesium in the presence of an inert organic solvent such as tetrahydrofuran (THF) or diethyl ether and then is condensed with (exo)octahydro-5,8-epoxy-1H-benzo-pyran-3-ol or (exo)octahydro-4,7-epoxyisobenzofuran-1-ol (prepared as described in U.S. Pat. No. 4,143,054) of the structure W

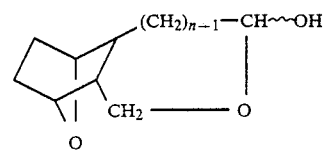  W employing a molar ratio of W:V of within the range of from about 1:2 to about 1:4, in the presence of an inert organic solvent such as THF at a reduced temperature of from about −78° to about 25° C., to form the condensed 7-oxabicycloheptane compound XV

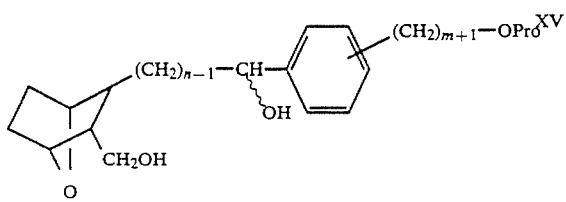

The condensed compound XV is then subjected to hydrogenolysis by treatment with hydrogen in the presence of a catalyst such as palladium hydroxide on charcoal in acetic acid or an inert organic solvent such as ethyl acetate, to form the alcohol XVI

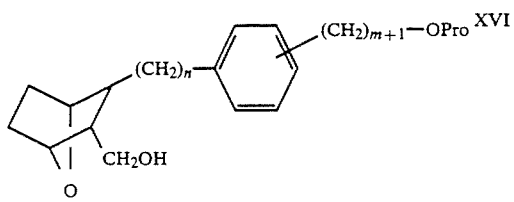

The alcohol function of alcohol XVI is protected by treatment, for example, with a solution of acetic anhydride, pyridine and 4-dimethylaminopyridine to form the protected alcohol XVII

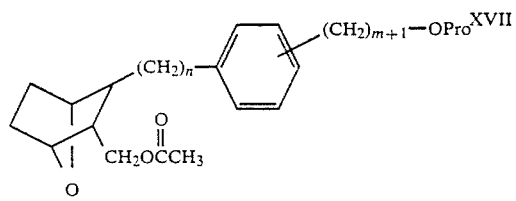

Alternatively, compound XVII can be protected by treatment with, for example, a solution of acetic anhydride and pyridine to form compound XVIII

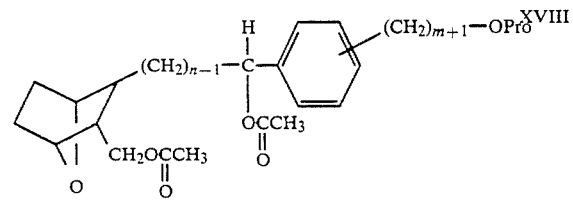

which is then subjected to hydrogenolysis as described above to provide compound XVII.

The protected alcohol XVII wherein Pro is t-butyldimethylsilyl or dimethyl(1,1,2-trimethylpropyl)silyl is subjected to a Jones oxidation emplying procedures described hereinbefore to form crude acid which is deacetylated by reaction with aqueous hydroxide in the presence of inert organic solvent such as THF and then esterified, for example, by treatment with diazoalkane, such as diazomethane, or acidic alcohol such as metanolic HCl, to form the alcohol ester XIX

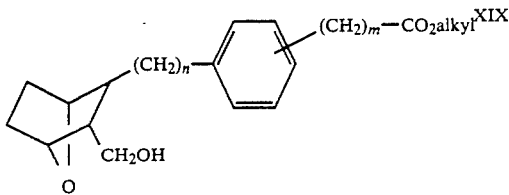

In an alternative method for forming alcohol ester XIX, protected alcohol XVIII is subjected to a Jones oxidation and esterification for form ester XX

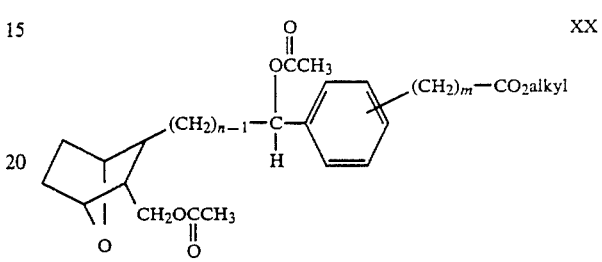

which is then made to undergo hydrogenolysis and subsequent removal of the acetate protecting group by transesterification to afford alcohol ester XIX.

Alcohol ester XIX is then tosylated by treatment of XIX with tosyl chloride in the presence of an organic base, such as pyridine or triethylamine, in the presence of an inert organic solvent such as methylene chloride, to form tosylate H.

Starting tosylate H wherein Z is

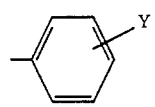

and Y is O may be prepared as follows:

Bromophenol $A^1$

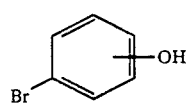

is treated with a protecting compound such as chloro-t-butyldimethylsilane, benzyl bromide or bromomethyl methyl ether, preferably benzyl bromide or bromomethyl methyl ether for orthobromophenol, employing conventional procedures to form the protected bromophenyl compound $B^1$

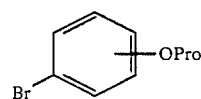

wherein Pro represents a protecting group.

Examples of protecting compounds suitable for use herein in reacting with bromophenol $A^1$ include those set out hereinbefore with respect to protection of alcohol U.

Protected compound $B^1$ is then transmetallated (using a procedure similar to that set out above with respect to transmetallation of V using n-butyllithium in THF) and condensed with hemiacetal W to form the condensed 7-oxabicycloheptane compound XXI

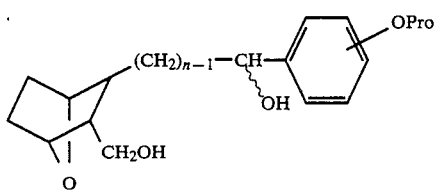   XXI

The condensed compound XXI is then subjected to hydrogenolysis by treatment with hydrogen in the presence of a catalyst such as palladium on charcoal in acetic acid, to form the alcohol XXII in the case where Pro is a silyl or methoxymethyl ether protecting group or to form XXV directly when Pro is benzyl.

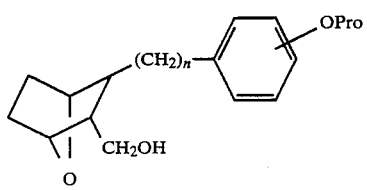   XXII

When Pro is a silyl protecting group, compound XXII is deprotected by treatment with, for example, a solution of acetonitrile and aqueous hydrofluoric acid to form the deprotected alcohol XXIII

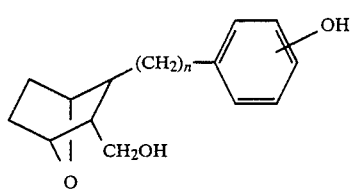   XXIII

The alcohol XXIII is then alkylated by treating a solution of alcohol XXIII in tetrahydrofuran with a molar equivalent of sodium hydride or one to four equivalents of a carbonate base such as potassium carbonate. The resulting phenoxide solution is alkylated by treating with a haloalkanoic acid ester C¹

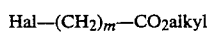   Hal—(CH₂)ₘ—CO₂alkyl   (C¹)

employing a molar ratio of C¹:XXIII of from about 1:1 to about 3:1, in the presence of an inert organic solvent such as THF or dimethylformamide or dimethoxyethane, to form ester XXIV

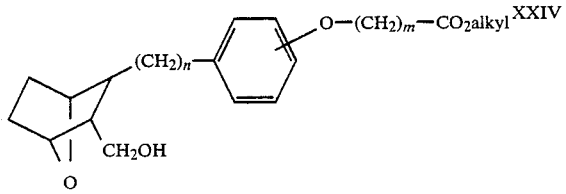   XXIV

Alternatively, when the protecting group in XXII is methoxymethyl, the free hydroxyl is protected as a benzyl ether. The methoxymethyl protecting group is removed by treatment with aqueous acid. The resulting phenol is alkylated with ethyl bromoacetate as described above for the alkylation of XXIII. The benzyl protecting group is then removed by hydrogenolysis with palladium hydroxide and hydrogen to give XXIV.

Alternatively, alcohol ester starting materials of formula XXIV may be prepared by following the procedure as described in U.S. Pat. No. 4,536,513.

Starting tosylate H where Z is

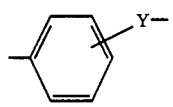

where Y is a single bond and m is 0, that is benzoic acids or derivatives thereof of the structure IU

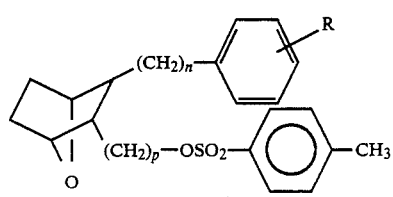   IU may be prepared starting with bromobenzyl alcohol D¹

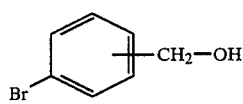   D¹ which is treated with a protecting compound such as t-butylchlorodiphenylsilane, in the presence of 4-dimethylaminopyridine and an amine base such as triethylamine and an inert solvent, such as methylene chloride, employing conventional procedures, to form the protected bromobenzyl compound E¹

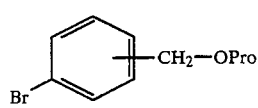   E¹ wherein Pro represents a protecting group.

Examples of protecting compounds suitable for use herein with the exclusion of benzyl bromide are as set out hereinbefore in reacting with bromophenalkyl alcohol U.

The protected compound E1 is then transmetallated by treatment with t-C₄H₉Li or n-C₄H₉Li in the presence of diethyl ether or tetrahydrofuran at reduced temperature of from about −100° to about 0° C. (or is subjected to a Grignard reaction by treatment with magnesium in the presence of an inert organic solvent such as tetrahydrofuran (THF) or diethyl ether) and then is condensed with (exo)octahydro-5,8-epoxy-1H-benzopyran-3-ol or (exo)octahydro-4,7-epoxyisobenzofuran-1-ol of the structure W employing a molar ratio of W:E¹ of within the range of from about 1:2 to about 1:4, in the presence of an inert organic solvent such as THF at a reduced temperature of from about −78° to about 25° C., to form the condensed 7-oxabicycloheptane compound XXV

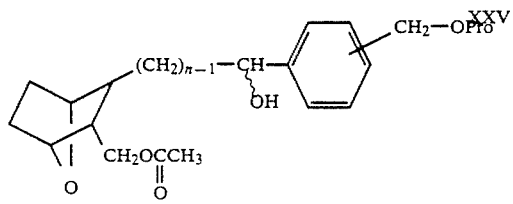

Compound XXV is then protected by treatment with, for example, a solution of acetic anhydride and pyridine in the presence of 4-dimethylaminopyridine to form compound XXVI

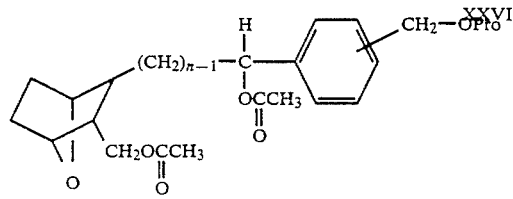

The protected alcohol XXVI is then deprotected using conventional procedures and the resulting alcohol subjected to a Jones oxidation employing procedures described hereinbefore to form crude acid. The crude acid is deacetylated by reaction with aqueous hydroxide in the presence of inert organic solvent such as THF and then esterified, for example, by treatment with diazoalkane, such as diazomethane, or acidic alcohol, to form the alcohol ester XXVII

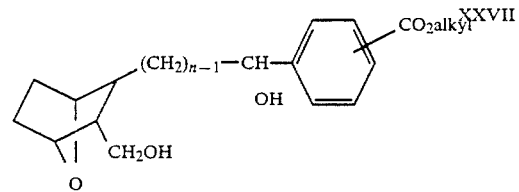

The alcohol ester is then subjected to hydrogenolysis as described above to provide alcohol ester compound XXVIII

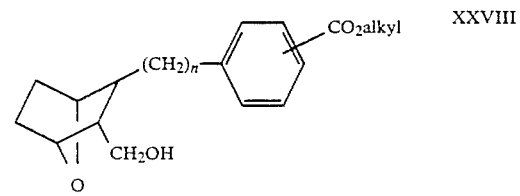

In a preferred method, compounds of the invention wherein m is 1, n is 1 and Y is a single bond, and R is in the ortho position, that is benzoic acids or derivatives thereof of the structure IW

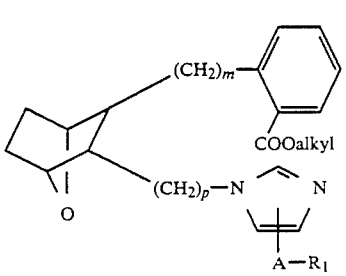

may be prepared starting with oxazoline

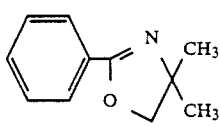

(prepared as described by A. I. Meyers el al, in J. Org. Chem. 39, 2787 (1974)) which is metallated by treatment with t-$C_4H_9Li$ or n-$C_4H_9Li$ in the presence of diethyl ether or tetrahydrofuran at reduced temperature of from about $-100°$ to about $0°$ C. and then is condensed with (exo) octahydro-4,7-epoxyisobenzofuran-1-ol (prepared as described in U.S. Pat. No. 4,143,054) of the structure $F^1$

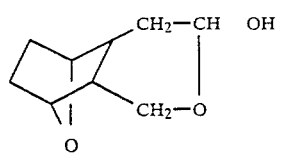

employing a molar ratio of $F^1$:oxazoline of within the range of from about 1:2 to about 1:4, in the presence of an inert organic solvent such as THF at a reduced temperature of from about $-78°$ to about $0°$ C., to form the condensed 7-oxabicycloheptane compound XXIX

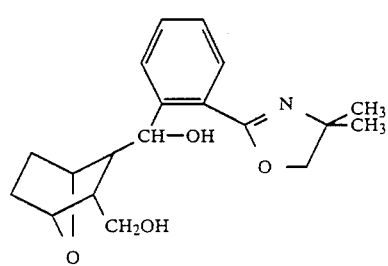

Compound XXIX is then subjected to aqueous acidic hydrolysis by treatment with aqueous oxalic acid to form compound XXX

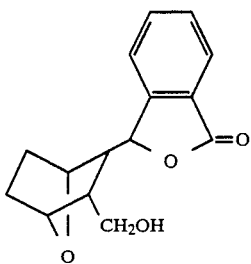

XXX

XXX is then subjected to hydrogenolysis as described above and esterification to provide alcohol ester compound XXXI

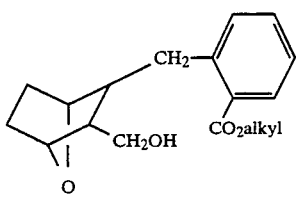

XXXI

Compound XXXI may be used in place of alcohol XIX to form compounds of the invention IW where m is 0 and n is 1.

Starting tosylate H where Z is —CH$_2$CH$_2$— may be prepared by reducing tosylate H where Z is —CH=CH— by treating same with a hydrogenation catalyst, such as palladium on charcoal, in the presence of an inert organic solvent, such as ethyl acetate or acetic acid.

The starting imidazole K in which A is attached at the 4 or 5 position of the imidazole ring may be prepared starting with acid G$^1$

G$^1$ which is treated with oxalyl chloride to form the corresponding acid chloride H$^1$

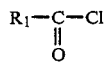

H$^1$

Acid chloride H$^1$ is treated with cyanotrimethyl silane under an inert atmosphere such as argon, at a temperature within the range of from about 20° C. to about 150° C., to form the nitrile J$^1$

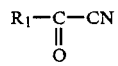

J$^1$

Nitrile J$^1$ is made to undergo reductive acylation by treating J$^1$ with a suspension of activated zinc dust in acetic anhydride and acetic acid, under an inert atmosphere such as argon, at a temperature within the range of from about 0° C. to about 75° C., to form K$^1$

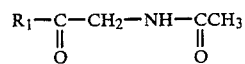

K$^1$ which is hydrolyzed by treating K$^1$ with hydrochloric acid under an inert atmosphere such as argon to form the amine hydrochloride L$^1$

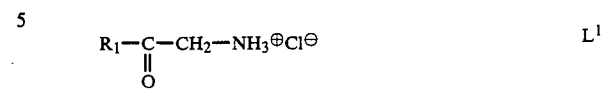

L$^1$

Compound L$^1$ is then cyclized by reacting L$^1$ with an aqueous solution of KSCN, at a temperature within the range of from about 20° C. to about 100° C., employing a molar ratio of L$^1$:KSCN of within the range of from about 1:1 to about 0.25:1, to form imidazole thiol M$^1$

M$^1$

M$^1$ is subjected to reductive desulfurization by treating M$^1$ with a suspension of Raney nickel or other reducing agent in the presence of an inert organic solvent such as methanol or ethanol, under an inert atmosphere such as argon, at a temperature within the range of from about 20° C. to about 90° C. to form the starting imidazole K.

The starting imidazole K in which R$_1$ is attached at the 2-position of the ring can be prepared by tretment of protected imidazole N$^1$ with a strong base, for example, n-butyllithium, in an inert solvent such as THF to form the anion which is condensed with an

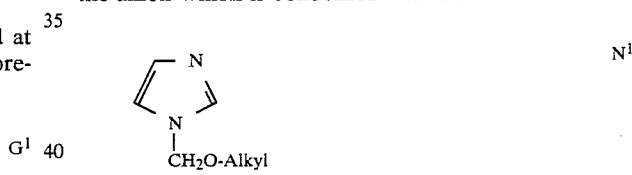

N$^1$

Hal-R$_1$

O$^1$ alkylating agent O$^1$ where Hal is a bromide, iodide or alkylsulfonate to form imidazole P$^1$ which is deprotected under standard conditions

P$^1$

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared by employing starting materials and following the procedures as outlined in U.S. Pat. No. 4,143,054. Examples of such stereoisomers are set out below.

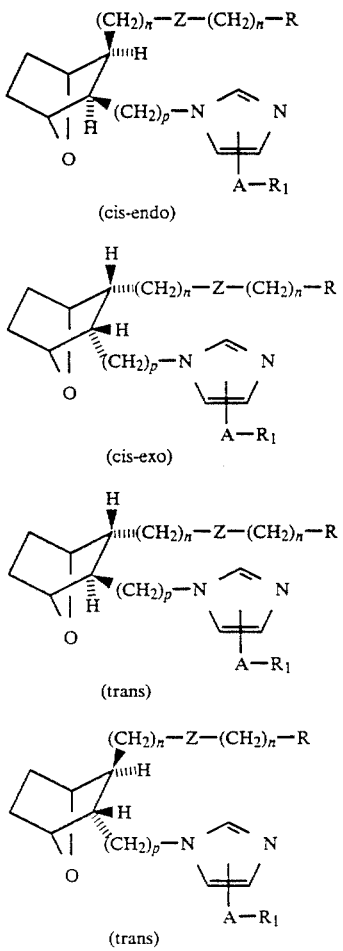

(cis-endo) Ia (cis-exo) Ib (trans) Ic (trans) Id

The nucleus in each of the compounds of the invention is depicted as

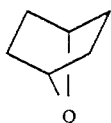

for matter of convenience; it will also be appreciated that the nucleus in the compounds of the invention may be depicted as

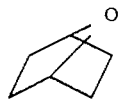

The compounds of this invention are thromboxane receptor antagonists and as such are useful as inhibitors of thromboxane receptor mediated actions, and are also thromboxane synthetase inhibitors. The term "thromboxane receptor antagonist" includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastasis, and tardive dyskinesia. The compounds may be useful in potentiating diureticinduced diuresis.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.1 to about 50 mg/kg and especially about 2 to 25 mg/kg (or from about 5 to about 2500 mg, preferably from about 10 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all tempertures are expressed in degrees Centigrade.

Example 1

[1S-[1α, 2α(Z),3α, 4α]]-6-[3-[[4-(4-Cyclohexyl-1-hydroxybutyl)-1H-imidazol-1-yl]methyl]-7-oxabicyclo-[2.2.1]hept-2-yl]-4-hexenoic acid, methyl ester

A. 1H-Imidazole-4-methanol

The free base of 4-(hydroxymethyl) imidazole was prepared by passing 10.00 g of the hydrochloride (74.31 mmol) through a column of 187 mL of analytical grade anion exchange resin (Bio-Rad AG 1-X8, 100–200 mesh, hydroxide form, 1.2 meg/mL of resin bed). Elution with water was carried out until the eluent was no longer basic and no more of the free base was visible by TLC (silica, 90/10 $CH_2Cl_2/CH_3OH$). Eluent volume was ca. 650 mL. Water was removed in vacuo and azeotroped with toluene to yield 7.21 g of a white crystalline solid:
$^1$H NMR ($CDC_3/CD_3OD$): δ7.53, s (1H); 7.35, s (1H); 6.93, s (2H); 3.76, br s.

B. 1H-Imidazole-4-carboxaldehyde

A solution of Part A imidazole (7.21 g, 74.3 mmol) in 360 mL of dioxane with 86.9 g of activated $MnO_2$ (220.5 mmol) was refluxed under argon for 40 minutes. After cooling to room temperature the suspension was filtered through a pad of Celite and rinsed with several portions of hot dioxane (55° C.); total rinse volume was 300 mL. Dioxane was removed in vacuo to yield 2.68 g of a white solid. The filter cake was rinsed with 300 mL each of boiling dioxane. Evaporation of the combined filtrates yielded an off-white solid which was combined with the above solid. The crude product was suspended in 50 mL of ethyl acetate, collected by filtration, rinsed with 25 mL of ethyl acetate then diethyl ether. Yield: 5.81 g of a white solid: mp 169°–170° C. dec.;
$^1$H NMR ($CDCl_3/CD_3OD$): δ9.80, s (1H); 7.81, s (1H); 7.79 s (1H); 3.75, br s (1H).

C. (3-Bromopropyl)cyclohexane

Title compound was prepared as described in Kamm, O; Marvel, C. S. in Organic Synthesis 1921, 1, 1–13, procedure G;
$^1$H NMR: δ3.38, t, J=7Hz (2H); 0.83–1.91, m (15H).
$^{13}$C NMR: δ37.0, 35.9, 34.2, 33.2, 30.4, 26.6, 26.3.

D. α-(3-Cyclohexylpropyl)-1H-imidazole-4-methanol

To a stirred suspension of Mg turnings (4.40 g, 181.1 mmol) in 117 mL of tetrahydrofuran (THF) (room temperature, under argon) was added a few drops of a solution of 30.96 g (150.9 mmol) of Part C bromide in 25 mL of THF. Initiation was verified by the addition of a crystal of $I_2$ which immediately decolorized. The remaining solution of Part C bromide was then added dropwise so as to maintain a gentle reflux. After completion of the addition, stirring was continued for 45 minutes. Compound Part C bromide was completely consumed by TLC (silica, 75/25 hexanes/ethyl acetate two times, PMA). Part B compound (5.80 g, 60.4 mmol) was added in several increments and did not dissolve well. Reflux was initiated for 1 minute after which time most of Part B compound dissolved and the reaction proceeded vigorously without external heat application for 90 minutes. Reflux was subsequently carried out for 20 minutes. Complete consumption of Part B compound was indicated by TLC. After cooling to room temperature, the reaction mixture was poured over 72 mL of 20% aqueous HCl solution (0° C.) and stirred for 5 minutes. THF was removed in vacuo, 200 mL of water were added, two extractions with 40 mL each of $CHCl_3$ were performed, and the reaction mixture was brought to pH 8.0 with 2M aqueous NaOH solution. The crude product was extracted 3 times with ethyl acetate (450 mL total), dried over $Na_2SO_4$ and concentrated to yield 13.33 g of an off-white sticky solid (99%). Trituration from 200 mL of diethyl ether (2 crops) yielded 12.57 g of a white crystalline solid: mp decomp >88° C.;
$^1$ NMR: δ9.29, br s (2H); 7.71 br s (1H); 6.85, br s (1H); 4.71, br s (1H); 1.78, br s (2H); 1.66, br s and 1.62, br s (5H); 1.41–1.15, m (8H); 0.83, m (2H).
$^{13}$C NMR: δ139.66, 134.68, 115.76, 66.49, 37.55, 37.62, 37.03, 33.34, 26.66, 26.35, 23.09.

E. 4-[4-Cyclohexyl-1-[[(1,1-dimethylethyl)-dimethylsilyl]oxy]butyl]-1H-imidazole Triethyl amine (0.66 mL, 4.7 mmol) was added to a solution of Part D compound (1.0 g, 4.5 mmol) and 1.02 g (6.75 mmol) of t-butyldimethylsilyl chloride in 50 mL of $CH_2Cl_2$ (room temperature, under argon). The initially cloudy solution was homogeneous after 24 hours reaction time. Methylene chloride was removed in vacuo and replaced with ethyl acetate. The ethyl acetate solution was washed 3 times with saturated aqueous $K_2CO_3$ solution, brine, dried over $Na_2SO_4$, and concentrated to yield 1.48 g of a viscous light yellow oil (98%). Flash chromatography on 100 g of silica gel (E. Merck Kieselgel 60, 200–400, mesh, 98/2 $CH_2Cl_2/CH_3OH$) yielded 1.31 g of a viscous colorless oil which very slowly crystallized to title compound in the form of a white solid upon standing:

¹H NMR: δ7.55, s (1H); 6.86, s (1H); 4.79, t (2H); 1.67–1.64, m (7H); 1.42–1.16, m (8H); 0.88, s and 0.88–0.80, m (11H); 0.06, s (3H); —0.06, s (3H).

¹³C NMR: δ134.33, 118.18, 68.71, 39.25, 37.55, 37.29, 33.34, 26.72, 26.40, 25.83, 22.49, 18.17, —4.86, —4.96.

F. [1S-[1α, 2α(Z),3α, 4α]-6-[3-[[4-[4-Cyclohexyl-1-[[(1,1-dimethylethyl)dimethylsilyl]-oxy]butyl]-1H-imidazol-1-yl]methyl]-7-oxabicyclo[2.2.1]hept-2-yl)-4-hexenoic acid, methyl ester A solution of 1.10 g of Part E compound (3.27 mmol) in 20 mL of dimethylsulfoxide (room temperature, under argon) was treated with 0.13 g of NaH (3.27 mmol of a 60% mineral oil dispersion). The NaH, added in several increments, was washed several times with pentane prior to the addition. Stirring at room temperature was continued for 30 minutes. The initally cloudy solution cleared up after 10 minutes. [1S-[1α, 2α(Z), 3α, 4α]]-6-[3-[[[(4-Methylphenyl)Methylphenyl)sulfonyl-]oxy]methyl]-7-oxabicyclo-[2.2.1]hept-2-yl]-4-hexenoic acid, methyl ester prepared as described in Example 9, Part E, was added in 1 portion (1.21 g, 2.97 mmol) and the reaction was run at 90° C. (oil bath temperature) for 4 hours. DMSO was removed with a vacuum pump/dry ice-cooled receiver flask. Ethyl acetate (50 mL) and 50 mL of water were added, the aqueous layer was extracted 2 times with 20 mL each of ethyl acetate, the combined ethyl acetate layers were washed with brine, dried over Na₂SO₄ and evaporated in vacuo to yield 1.76 g of a viscous yellow oil (>100%). Flash chromatography on 100 g of silica gel (E. Merck Kieselgel 60, 240–400 mesh) yielded 0.88 g of a viscous yellow oil:

¹H NMR: δ7.47, s; 7.40 (1H); 6.78, s (1H); 5.42–5.35 (3H); 4.72, t (1H); 4.27–4.09, m (2H); 3.95–3.88, m (1H); 3.79, t, J=11.14Hz (1H); 3.67, s (3H); 2.39, s (4H); 2.33–1.97, m (1H); 1.68–1.64, (m 8H); 1.49–1.16, m (7H); 0.95–0.83, m, 0.89, s, and 0.88, s (9H); 0.06, s, 0.00, s, —0.46, —0.06, s and 0.01 and —0.10, m (7H).

G. [1S-[1α, 2α(Z),3α, 4α]]-6-[3-[[4-(4-Cyclohexyl-1-hydroxybutyl)-1H-imidazol-1-yl]methyl]-7-oxabicyclo[2.2.1]hept-2-yl]-4-hexenoic acid, methyl ester A solution of Part F compound (0.59 g, 1.0 mmol) in 20 mL of methanol (room temperature, under argon) was treated with 0.50 mL of acetyl chloride (5.5 mmol). Stirring was continued for 1 hour. TLC (silica, 90/10 CH₂Cl₂/CH₃OH) indicated an incomplete reaction. An additional portion of acetyl chloride was added and stirring continued for 90 minutes. Methanol was removed in vacuo. The residue was dissolved in 20 mL of ethyl acetate, washed 2 times with 30 mL each of saturated aqueous KHCO₃ solution, brine, dried over Na₂SO₄ and concentrated to yield 0.50 g of a viscous tan oil. Flash chromatography on 35 g of silica gel (E. Merck Kieselgel 60, 240–400 mesh) yielded 0.29 g of a colorless oil. The product was eluted with 97/3 CH₂Cl₂/CH₃OH after all upper R_f by-products had been eluted with 99/1 CH₂Cl₂/CH₃OH. Yield: 0.61 g of title compound in the form of a colorless oil:

¹H NMR: δ7.45, s (1H); 6.83, s (1H); 5.43–5.34, m (2H); 4.64, br t (1H); 4.27, d, J=4.11 Hz (1H); 4.15, d, J=4.11 Hz (1H); 3.96, dd, J=4.69 Hz, J=13.48 Hz (1H); 3.81, t, J=13.48 Hz (1H); 3.67, s (3H); 3.58, br m (1H); 2.39, s (4H); 2.29–2.00, m (4H) 1.97–1.76, m (2H); 1.70–1.65, m (7H); 1.49–1.37, m (4H); 1.23–1.19, m (6H); 0.86, m (2H).

¹³C NMR: δ173.21, 146.28, 136.47, 129.38, 129.21, 114.49, 80.46, 78.44, 68.30, 51.40, 47.77, 46.13, 46.02, 37.41, 37.20, 37.09, 33.58, 33.23, 29.54, 28.85, 26.58, 26.26, 25.97, 22.89, 22.83.

EXAMPLE 2

[1S-[1α, 2α(Z),3α, 4α]]-6-[3-[[4-(4-Cyclohexyl-1-hydroxybutyl)-1H-imidazol-1-yl]methyl]-7-oxabicyclo-[2.2.1]hept-2-yl]-4-hexenoic acid A solution of 0.29 g of Example 1 compound (0.63 mmol) in 3.0 mL of CH₃OH was treated with 0.35 g of KOH (6.3 mmol) then 2.5 mL of water (room temperature, under argon). The initially cloudy reaction mixture turned clear after 10 minutes. Stirring was continued for 1 hour and 20 minutes. Methanol was removed in vacuo. Water (2.0 mL) was added followed by 1M aqueous HCl solution to pH 1.0. Water was removed in vacuo. The residue was azeotroped with toluene. The residue was treated with 20 mL of 50/50 CH₂Cl₂/CH₃OH; insoluble salts were removed by filtration. The filtrate was concentrated and the above process repeated. The crude product after solvent removal contained some unreacted Example 1 compound. Hydrolysis of Example 1 compound was carried out again under the same conditions overnight. Workup procedure yielded 0.27 g of an off-white glass (96%), free of Example 1 compound by TLC. Flash chromatography on 20 g of silica gel (E. Merck Kieselgel 60, 240–400 mesh, 90/10 ethyl acetate-PAW*) yielded 0.23 g of a viscous colorless oil. The oil was dissolved in 2.0 mL of CHCl₃ and filtered through a millipore filter (Gelman Acrodisc CR PTFE 0.45 μm), and evaporated in vacuo to yield an oil which was washed 3 times with 90/10 hexanes/ether (decanted off). Yield after solvent removal: 0.20 g of title compound as a white glassy solid;
*PAW=20/6/11 pyridine/acetic acid/H₂O ¹H NMR: δ9.10, br s (2H); 7.62, s (1H); 6.81, s (1H); 5.47–5.34, m (2H); 4.59, t (1H); 4.29, d (1H) and 4.10, d (1H), J=3.52 Hz; 3.95, dd, J=13.5 Hz, J=4.69 Hz (1H); 3.82, t, J=13.50 Hz (1H); 2.45–2.33, m and br d (4H); 2.26–1.93, m (4H); 1.80–1.65, m (9H); 1.49–1.43, m (1H); 1.35–1.09, m (9H); 0.93–0.83, m (2H).

¹³C NMR: δ171.36, 144.91, 136.27, 130.10, 129.15, 115.19, 80.86, 78.47, 67.30, 47.86, 46.71, 46.33, 37.58, 37.26, 36.63, 34.67, 33.38, 29.78, 28.84, 26.75, 26.44, 26.29, 23.41, 23.18.

Anal. calc'd for C₂₆H₄₀N₂O₄.0.40H₂O.0.25HCl:

|  | C, | 67.69; | H, | 8.98; | N, | 6.07; | Cl, | 1.92 |
|---|---|---|---|---|---|---|---|---|
| Found: | C, | 67.85; | H, | 8.88; | N, | 5.91; | Cl, | 2.10. |

EXAMPLE 3

[1S-[1α, 2α(Z),3α, 4α]]-6-[3-[[4-(3-Cyclohexylpropyl)-1H-imidazol-1-yl[methyl[-7-oxabicyclo[2.2.1][hept-2-yl]-4-hexonoic acid, methyl ester A. Cyclohexanebutanoyl chloride To a solution of 15.0 g (0.088 mol) of cyclohexanebutyric acid in 30 mL of CH₂Cl₂ (0° C. ice bath, under an argon stream) was added dropwise 8.45 mL (0.097 mol) of oxalyl chloride over 5 minutes. Vigorous gas evolution was observed shortly after completion of the oxalyl chloride addition. The reaction was run overnight at room temperature. An infrared scan of the reaction mixture indicated the presence of some unconverted acid. Dimethyl formamide (DMF) was added (20 drops) at room temperature (which caused immediate gas evolution) and the reaction was continued at room temperature for 45 minutes. Solvent was removed in vacuo to yield a light yellow oil.

B. α-Oxocyclohexanepentanenitrile

A solution of 47.1 mL (0.37 mol) of cyanotrimethyl silane in 58.44 g (0.31 mol) of Part A acid chloride was heated to 100° C. (oil bath temperature) for 6 hours under argon. Reaction progress was monitored by infrared spectrometry (CHCl$_3$ solution). The reaction was carried out in a round-bottom flask fitted with a reflux condenser. Chlorotrimethylsilane was removed with a vacuum pump/dry ice-cooled receiver flask. Yield: 58.78 g of a red oil (title compound with some unremoved chlorotrimethylsilane):

$^{13}$C NMR (CDCl$_3$, ref 77.0): δ177.07, 113.26, 45.31, 37.24, 36.26, 33.07, 26.51 26.18, 20.23

C. N-(5-Cyclohexyl-2-oxopentyl)acetamide

To a stirred suspension of 50.28 g of activated zinc dust (0.77 mol) in 126 mL of acetic anhydride/126 mL of acetic acid under argon was added dropwise over 30 minutes a solution of 15.77 g (0.088 mol) of Part B compound in 17 mL of acetic anhydride/17 mL of acetic acid. The reaction temperature during and after the addition was maintained at 45° C. (oil bath temperature). Reaction time was 4.5 hours. TLC (silica, 50/50 hexanes/ ethylacetate) indicated complete conversion of Part B compound to product. The reaction mixture was cooled to room temperature, filtered through a pad of Celite, and rinsed with several portions of CH$_2$Cl$_2$. Removal of the solvents in vacuo (with several portions toluene as azeotrope) yielded 18.71 g of a yellow oil (94%). Flash chromatography on 750 g of E. Merck Kieselgel 60 silica gel (240–400 mesh) yielded 5.43 g of a white crystalline solid. The desired title product was eluted with 2L of 85/15 ethyl acetate-hexanes then ethyl acetate; upper-R$_f$ by-products were eluted with 50/50 hexanes/ethyl acetate then 2L of 75/25 ethyl acetate/hexanes: mp 76.5°–78.5° C.;

$^{13}$C NMR (CDCl$_3$, ref 77.21): δ205.91, 170.35, 49.55, 40.94, 39.78, 37.65, 37.15, 33.45, 26.86, 26.54, 23.17, 21.41

D. 1-Amino-5-cyclohexyl-2-propanone, monohydrochloride

A cloudy solution of Part C compound (14.97 g, 66.44 mmol) in 550 mL 4N HCl/139 mL tetrahydrofuran (THF) was refluxed under argon for 8.5 hours. The reaction mixture gradually became a clear yellow solution. THF and water were removed in vacuo (azeotroped with toluene). Trituration of the residue with 400 mL of diethyl ether yielded 13.87 g of title compound in the form of an off-white solid: mp 141°–162° C. dec.;

$^{13}$C NMR (CDCl$_3$/CD$_3$OD, ref 77.00): δ47.53, 40.49, 37.35, 36.75, 33.17, 26.51, 26.24, 20.39

E. 4-(3-Cyclohexylpropyl)-1H-imidazole-2-thiol

A solution of KSCN (1.93 g, 19.9 mmol) in 20 mL of water was treated with 3.36 g of Part D compound (15.3 mmol). The reaction was run at 82° C. (oil bath temperature) for 4.5 hours. Within 10 minutes of heating, all of Part D compound dissolved to form a clear deep yellow solution. Product precipitation was first observed after c.a. 1 hour reaction time. The crude product was collected by filtration, rinsed several times with c.a. 25 mL total of water then 0° C. chilled diethyl ether (50 mL total) to yield 2.66 g of title compound in the form of white crystalline plates: mp 176°–177° C.;

$^{13}$C NMR (CDCl$_3$, ref 77.00): δ157.56, 131.12, 111.13, 37.24, 36.64, 33.33, 26.56, 26.24, 25.53, 24.99

F. 4-(3-Cyclohexylpropyl) -1H-imidazole

A suspension of 11.0 g of W-2 Raney nickel in a somewhat cloudy solution of 2.30 g of Part E compound (10.25 mmol) in 100 mL of absolute methanol was refluxed under argon for 2.5 hours. After cooling to room temperature, the reaction mixture was filtered through a pad of Celite, rinsed with c.a. 30 mL each of absolute ethanol, methanol, then water. Evaporation of filtrate in vacuo (azeotroped 2 times with toluene then coevaporated with diethyl ether) yielded 1.72 g of an off-white solid (87%). The crude product was partitioned between ethyl acetate and 25 mL of 2M aqueous trisodium citrate solution. After separation of the layers, the ethyl acetate layer was washed 2 times with 25 mL total of the above citrate solution (pH 8.5), brine, dried over Na$_2$SO$_4$ and evaporated in vacuo to yield 1.63 g of an oil which slowly crystallizes upon standing. The solid was suspended in 30 mL of hexanes, collected by filtration and rinsed with c.a. 20 mL of hexanes. Yield: 1.60 g of title compound in the form of a white crystalline solid: mp 81°–82° C.;

$^{13}$C NMR (CDCl$_3$, ref 77.00): δ136.78, 134.22, 117.86, 37.49, 37.12, 33.32, 26.89, 26.75, 26.66, 26.35

G. [1S-[1α,2α(Z),3α,4α]]-6-[3-[[4-(3-Cyclohexylpropyl)-1H-imidazol-1-yl]methyl]-7-oxabicyclo[2.2.1]hept-2-yl]-4-hexenoic acid, methyl ester A solution of 0.71 g of Part F compound (3.7 mmol) and 0.50 g of [1S-[1α, 2α(Z),3α, 4α]]-6-[3-(tosyloxymethyl)-7-oxabicyclo[2.2.1]hept-2-yl]-4-hexenoic acid, methyl ester prepared as described in Example 9, Part E (1.2 mmol) in 2.0 mL of anhydrous DMF was stirred at 115° C. (oil bath temperature) overnight under argon. DMF was removed with a vacuum pump-dry ice-cooled receiver flask. Ethyl acetate (30 mL) and water (15 mL) were added, the ethyl acetate layer was washed with water (15 mL), brine, dried over Na$_2$SO$_4$ and concentrated to yield 1.39 g of a dark tan viscous oil. Recrystallization from ethyl acetate (1 crop, seeded with Part F compound) yielded 0.25 g of an off-white crystalline solid, the tosylate salt of Part F compound. The filtrate (0.82 g of a yellow oil) was flash chromatographed on 30 g of E. Merck Kieselgel 60 silica gel (240–400 mesh, 99/1 CH$_2$Cl$_2$/CH$_3$OH then 95/5 CH$_2$Cl$_2$/CH$_3$OH after most of the desired product has been eluted) to yield 0.25 g of title compound in the form of a light yellow viscous oil:

$^{13}$C NMR (CDCl$_3$, ref 77.00): δ173.01, 143.49, 135.95, 129.35, 129.01, 114.46, 80.28, 78.33, 51.20, 47.66, 46.02, 45.70, 37.26, 36.94, 33.46, 33.11, 29.40, 28.77, 28.48, 26.40, 26.12, 25.86, 22.69

EXAMPLE 4

[1S-[1α, 2α(Z),3α, 4α]]-6-[3-[[4-(3-Cyclohexylpropyl)-1H-imidazol-1-yl]methyl]-7-oxabicyclo[2.2.1]hept-2-yl]-4-hexenoic acid A solution of 0.25 g of Example 3 compound (0.58 mmol) in 3.0 mL of methanol was treated with 0.33 g (5.83 mmol) of KOH then 1.4 mL of water. Stirring of the clear yellow solution was continued under argon for 4.5 hours. 1 M HCl was added to pH 1.0. Methanol and water were removed in vacuo. The crude product was dissolved in 40 mL of 1:1 methanol-methylene chloride and insoluble salts were removed by filtration. The filtrate was concentrated and the above process repeated. Removal of the solvents in vacuo yielded 0.28 g of a light yellow taffy. Flash chromatography on 28 g of E. Merck Kieselgel 60 silica gel (240–400 mesh, 95/5 ethyl acetate/PAW) followed by treatment of the residue 3 times with 3.0 mL each of 75/25 hexanes/diethyl ether and decanting yielded 0.13 g of title product in the form of a viscous yellow oil. The product was dissolved in 2.0 mL of ethyl acetate, filtered through a milipore filter, and evaporated. The above process was repeated once. Yield after solvent removal: 80.9 mg of hard yellow taffy:

$^{13}$C NMR (CDCl$_3$,ref 77.00): δ141.59, 136.18, 130.10, 129.12, 115.24, 80.78, 78.64, 47.89, 46.77, 46.42, 37.46, 37.06, 34.56, 33.38, 29.75, 28.80, 27.53, 26.72, 26.41, 26.32, 26.23, 23.35

$^1$H NMR (CDCl$_3$,ref TMS): δ7.81, s (1H); 6.64, s (1H); 5.47–5.40, m (2H); 4.29, d, J≈4.1 Hz (1H); 4.13, d, J≈4.1 Hz (1H); 3.96, dd, J=14.1 Hz, J=4.69 Hz (1H); 3.82, dd, J=14.1 Hz, J=11.7 Hz (1H); 2.54, t (2H); 2.38, m (4H); 2.23–1.97, m (3H); 1.67, m (8H); 1.48–1.37, m (4H); 1.20, m (5H); 0.88, m (2H).

Anal. calc'd for C$_{25}$H$_{38}$N$_2$O$_3$.0.7HC1.0.5H$_2$O:

|       | C,    | H,   | N,   | Cl,  |
|-------|-------|------|------|------|
|       | 66.87; | 8.91; | 6.24; | 5.53 |
| Found: | C, 66.90; | H, 8.51; | N, 5.99; | Cl, 5.59. |

EXAMPLE 5

[1S-[1α, 2α(Z), 3α, 4α]]-6-[3-[[4-(4-Cyclohexyl-1-oxobutyl)-1H-imidazol-1-yl]methyl]-7-oxabicyclo-[2.2.1]hept-2-yl]-4-hexenoic acid, methyl ester A solution of 0.50 g of Example 1 compound (1.09 mmol) with a suspension of 0.28 g of activated MnO$_2$ (3.0 eq.) in 15 mL of dioxane was refluxed under argon for 3 days. Reaction progress was slow, with repeated additions of MnO$_2$ necessary to drive the oxidation to completion (total amount of MnO$_2$ added was 13.5 eq., 0.14 g at a time). The reaction mixture was filtered through a pad of Celite and rinsed with boiling dioxane until no more product was visible by TLC in the filtrate (100 mL). Dioxane was removed in vacuo and replaced with 15 mL of ethyl acetate. The ethyl acetate solution was rinsed with 3 mL of 2M trisodium citrate solution, brine, dried over Na$_2$SO$_4$ and evaporated to yield 0.50 g of a viscous tan oil (>100%). The crude product was absorbed on Celite and filtered through a small pad of Florisil (2.4×2.2 cm); the pad was rinsed with hexanes and the desired product eluted with 95/5 ethyl acetate/CH$_3$OH. Yield: 0.41 g of title compound in the form of a yellow oil. NMR data indicated a small amount of impurity present:

$^1$H NMR (CDCl$_3$,ref TMS): δ 7.54, d, J=1.76Hz (1H); 7.44, d, J=1.17 Hz (1H); 5.35, m (2H); 4.21, d (1H) and 4.05, d, J=4.10 Hz (1H); 3.93, dd, J=13.49 Hz and J=4.69Hz (1H); 3.83, t, J=13.49Hz (1H); 3.60 s (3H); 2.88, t, J=11.14 Hz (2H); 2.32, br s (4H); 2.24–1.71, m (4H); 1.66–1.58, m (9H); 1.44–1.30, m (2H); 1.22–1.10, m (6H); 0.82–0.78, m (2H)

$^{13}$C NMR (CDCl$_3$, ref 77.00): δ 196.52, 172.95, 142.56, 137.29, 129.26, 129.09, 122.50, 80.35, 78.09, 51.25, 47.65, 46.39, 46.00, 38.75, 37.19, 36.85, 33.39, 33.00, 29.43, 28.67, 26.45, 26.11, 25.97, 22.71, 21.31.

EXAMPLE 6

[1S-[1α, 2α(Z), 3α, 4α]]-6-[3-[[4-(4-Cyclohexyl-1-oxobutyl)-1H-imidazol-1-yl]methyl]-7-oxabicyclo-[2.2.1]hept-2-yl]-4-hexenoic acid A cloudy solution of 0.41 g of Example 5 compound (0.90 mmol) and 9.0 mL of 1M aqueous LiOH solution in 39 mL of THF/7.8 mL of water was stirred at room temperature for 2.5 hours. THF was removed in vacuo. The aqueous gum was extracted 6 times with 15 mL each of CHCl$_3$. The combined CHCl$_3$ layers were washed with brine, dried over Na$_2$SO$_4$ and evaporated in vacuo to yield 0.28 g of alight yellow taffy (70%). TLC indicated no product remained in the aqueous layer. Flash chromatography on 25 g of silica gel (E. Merck Kieselgel 60, 240–400 mesh, 99/1 ethyl acetate/PAW) yielded 0.28 g of title compound in the form of a viscous light yellow taffy. The product was washed 2 times with 5 mL each of hexanes at 0° C.; the hexanes were decanted off. Removal of residual hexanes yielded 0.25 g of title compound in the form of a light yellow viscous taffy.

$^1$H NMR (CDCl$_3$,ref TMS): δ 10.78, br s (1H); 7.60, br s (1H); 7.56, br s (1H); 5.40–5.34, m (2H); 4.20, d (1H) and 4.10, d (1H), J=4.11 Hz; 3.96, dd, J=11.14 Hz and J=4.69 Hz (1H); 3.86, t, J=11.14 Hz (1H); 2.83, t, J=7.13 Hz (2H); 2.34, br s (4H); 2.21–1.94, m (4H); 1.61–1.58, m (9H); 1.44–1.30, m (2H); 1.18–1.12, m (6H); 0.81, m (2H).

$^{13}$C NMR (CDCl$_3$, ref 77.00): δ 196.42, 176.61, 141.96, 137.96, 129.64, 129.12, 122.96, 80.63, 78.32, 77.46, 47.80, 46.71, 46.16, 39.05, 37.38, 36.97, 33.69, 33.17, 29.54, 28.79, 26.58, 26.26, 26.12, 22.83, 21.42.

Anal. calc'd for C$_{26}$H$_{38}$N$_2$O$_4$.0.75HCl:

|       | C,    | H,   | N,   | Cl,  |
|-------|-------|------|------|------|
|       | 66.44; | 8.31; | 5.96; | 5.68 |
| Found: | C, 66.57; | H, 8.14; | N, 5.76; | Cl, 5.76. |

EXAMPLE 7

[1S-[1α, 2α(Z),3α4α]]-6-[3-(1H-Imidazol-1-ylmethyl)-7-oxabicyclo[2.2.1]hept-2-yl]-4-hexenoic acid, methyl ester A solution of 0.60 g of the tosylate employed in Example 3, Part G (1.47 mmol) with 0.30 g of imidazole (4.4 mmol) in 1.2 mL of dry DMF under argon was reacted at 110° C. (oil bath temperature) overnight. Dimethylformamide (DMF) was removed with a vacuum pump/dry ice-cooled receiver flask. Ethyl acetate and aqueous 10% KHCO$_3$ solution were added, the ethyl acetate layer was washed 3 times with 10% aqueous KHCO$_3$ solution, 15 3 times with water, brine, dried over Na$_2$SO$_4$ and evaporated in vacuo to yield 0.37 g of a yellow oil (83%). Flash chromatography on 50 g of silica gel (E. Merck Kieselgel 60, 240–400 mesh) yielded 0.24 g of title product in the form of a viscous yellow oil. The product was eluted with 97/3 CH$_2$Cl$_2$/CH$_3$OH after all upper-R$_f$ by-products were eluted with 99/1 CH$_2$Cl$_2$/CH$_3$OH:

$^{13}$C NMR (CDCl$_3$,ref 77.00): δ 173.04, 136.96, 129.41, 129.26, 129.09, 118.61, 80.31, 78.27, 51.28, 47.74, 46.02, 45.81, 33.46, 29.40, 28.74, 25.86, 22.69

$^1$H NMR (CDCl$_3$,ref TMS): δ 7.51, s (1H); 7.07, s (1H); 6.96, s (1H); 6.96–5.40, m (2H); 4.28, d, J=4.11 Hz (1H); 4.14, d, J=4.11 Hz (1H); 3.98, dd, J=11.14 Hz, J=4.69 Hz (1H); 3.87, t, J=11.14 Hz, (1H); 3.67, s (3H); 2.39, br s (4H); 2.32–2.25, m (2H); 2.23–1.99, m (2H); 1.69, m (2H); 1.50–1.26, m (2H).

EXAMPLE 8

[1S- [1α, 2α(Z),3α, 4α]]-6-[3-(1H-Imidazol-1-ylmethyl)-7-oxabicyclo[2.2.1-]hept-2-yl]-4-hexenoic acid A solution of 0.15 g of Example 7 ester (0.49 mmol) and 0.28 g of KOH (4.9 mmol) in 1.2 mL of water/2.5 mL of methanol was stirred at room temperature under argon for 4.5 hours. Methanol was removed in vacuo and 1M HCl was added to pH 1.0. Water was removed in vacuo, azeotroped with toluene. The residue was suspended in 40 mL of 50/50 CH$_2$Cl$_2$/CH$_3$OH, filtered through a pad of Celite, and rinsed with 2×20 mL portions 50/50 CH$_2$Cl$_2$/CH$_3$OH. The filtrate was concentrated to yield 0.20 g of a yellow taffy which was suspended in hexanes 3 times (5 mL each, decanted off). Flash chromatography on 20 g of silica gel (E. Merck Kieselgel 60, 240–400 mesh, 5/1 ethyl acetate/PAW) yielded 69.0 mg of a hard tan taffy. The product was dissolved in 2.4 mL of ethyl acetate and filtered through a millipore filter. The above process was repeated on the filtrate. Yield after concentration of the filtrate: 30.0 mg of title compound in the form of a hard tan taffy which very slowly solidified to a white solid upon standing:

$^{13}$C NMR (CDCl$_3$,ref 77.00): δ130.16, 129.10, 80.80, 78.50, 48.06, 46.59, 46.39, 29.75, 28.97, 26.26, 23.35

$^1$H NMR (CDCl$_3$,ref TMS): δ12.41, br s (1H); 7.73, br s (1H); 7.12, br s (1H); 6.96, br s (1H); 5.48–5.41, m (2H); 4.30, br s (1H); 4.11, br s (1H); 3.95, br dd (1H). 3.88, br t (1H); 2.40, br s (4H); 2.24–1.99, m (4H); 1.68, br s (2H); 1.49–1.34, m (2H).

Anal. calc'd for C$_{16}$H$_{22}$N$_2$O$_3$.0.06HCl.0.43H$_2$O:

|  | C, | 63.98; | H, | 7.69; | N, | 9.33; | Cl, | 0.71 |
|---|---|---|---|---|---|---|---|---|
| Found: | C, | 64.06; | H, | 7.73; | N, | 8.80; | Cl, | 0.78. |

EXAMPLE 9

[1S-[1α, 2α(Z),3α, 4α]]-6-[3-[[4-[[(4-Cyclohexylbutyl)amino]carbonyl]-1H-imidazol-1-yl]methyl]-7-oxabicyclo[2.2.1]hept-2-yl]-4-hexenoic acid, methyl ester All chromatographies were performed with E. Merck Kieselgel 60 silica gel (240–400 mesh).

A. 1H-Imidazole-4-carboxylic acid

Compound A was prepared according to the method of Cohen, David, & Kirk (J. Het. Chem., 19, 253 (1982)).

B. 4-Cyclohexylbutylamine hydrochloride

To a stirred solution of 4-phenylbutylamine (10.6 g, 71.1 mmol, Aldrich) in 100 mL of glacial acetic acid under argon was added 87% PtO$_2$ (1.06 g, 10% weight based on 4-phenylbutylamine). The reaction mixture was hydrogenated at 54 psi at room temperature for 4 hours. The catalyst was removed by filtration through a 2" pad of Celite, and the filtrate was concentrated in vacuo. The residue was diluted with 200 mL of diethyl ether, 100 mL of CH$_3$OH and 8 mL of concentrated HCl. This mixture was concentrated in vacuo and triturated in diethyl ether to give 13.1 g (97%) of desired amine.HCl.

C. [1S-[1α, 2α(Z), 3α, 4α]]-6-[3-(Hydroxymethyl)-7-oxabicyclo[2.2.1]hept-2-yl]-4-hexenoic acid, methyl ester To a partial solution of 36.27 g of (endo)-octahydro-5,8-epoxy-1H-benzo[c]pyran-3-ol (prepared as described in U.S. Pat. No. 4,143,054) (0.23 mol) and 3-carboxypropyltriphenylphosphonium bromide (127.34 g, 0.37 mol) in 600 mL of dry THF under argon at 3° C. was added dropwise over 1 hour a solution of 370.6 mL of potassium t-amylate (0.68 mol of a 1.8M toluene solution) with mechanical stirring. Initially the reaction temperature reached a maximum of 8° C. and subsequently leveled off to 4° C. for the remainder of the base addition. The reaction was then run at room temperature for 90 minutes. A 0° C. ice bath was introduced and the reaction was quenched by the addition of 152 mL of glacial acetic acid, over 30 minutes. Solvents were removed in vacuo (azeotroped with toluene). Water (640 mL) and 50 mL of concentrated HCl were added (pH 2.6). Dilution with 640 mL of ethyl acetate, the addition of 149 g of NaCl and a few seed crystals of 3-carboxypropyltriphenylphosphonium bromide was followed by vigorous stirring for 15 minutes. The precipitate was collected by filtration and washed with 2 portions each of 320 mL of ethyl acetate. The ethyl acetate layer was separated, the aqueous layer was extracted with ethyl acetate (2×200 mL each), the combined ethyl acetate layers were dried over MgSO$_4$ and concentrated. Aqueous 5% K$_2$CO$_3$ was added (507 mL) followed by vigorous stirring for 1 hour. No precipitation occurred. The reaction mixture was concentrated to a paste and suspended in 508 mL of water. Several hours of vigorous stirring produced no precipitate. The water was decanted off and the residue was suspended in 200 mL of aqueous 5% K$_2$CO$_3$ solution. After vigorous stirring, a light tan solid was collected by filtration and rinsed several times with water. The combined aqueous layers were extracted 5 times with 1:1 toluene/ diethyl ether (230 mL each). After cooling the combined aqueous layers with a 0° C. ice bath, concentrated HCl was added to pH 2.5, followed by extraction once with 460 mL then 2 times with 230 mL each of ethyl acetate. The combined ethyl acetate layers were dried over MgSO$_4$ and evaporated in vacuo to yield 49.74 of an amber oil. Trituration from 330 mL of diethyl ether (room temperature, overnight) oiled out phosphorous by-products. The ether solution was decanted away from the dark red oil into a separatory funnel, and the oil which was carried over by the decantation was drained off (1.56 g). Evaporation of the ether solution in 0 vacuo yielded 43.08 g of [1S-[[1α, 2α(Z),3α, 4α]]-6-[3-(hydroxymethyl)-7-oxabicyclo[2.2.1]hept-2-yl]-4-hexenoic acid in the form of a viscous yellow oil.

$^1$H NMR indicated a product: triphenylphosphine oxide: ether molar ratio of 23:1:1.8 (mass % 93:4.7:2.2). Yield exclusive of triphenylphosphine oxide/ether, 40.06 g (72.5%).

Acetyl chloride (5.20 mL, 0.073 mol) was added dropwise to 80 mL of methanol at room temperature under argon. The acetyl chloride/methanol solution was then added to a solution of 42.98 g (0.18 mol) of the preceding acid in 700 mL of methanol in one portion. Stirring was continued for 3 hours. Triethylamine was added (0.09 mol, 12.21 mL), methanol was removed in vacuo, and the residue was partitioned between 300 mL of ethyl acetate and 150 mL of water. After separation of the layers, the aqueous layer was extracted with 150 mL of ethyl acetate, the combined ethyl acetate layers were washed with brine, dried over $Na_2SO_4$ and evaporated in vacuo to yield 43.06 g of a viscous tan oil. Flash chromatography on 1350 g of E. Merck Kieselgel 60 silica gel (240–400 mesh, 75/25 diethyl ether/hexanes, then diethyl ether after the desired product began eluting off the column) yielded 35.74 g title ester in the form of a viscous light yellow oil, free from triphenylphosphine oxide by NMR.

$^1$H NMR (CDCl$_3$,ref. TMS): δ5.41–5.38, m (2H); 4.49, d, J=4.69 Hz (1H); 4.22, d, J=4.69 Hz (1H); 3.73–3.69, m (1H); 3.67, s, (3H); 3.60, m (1H); 2.37, br s (4H); 2.12–1.99, m (3H); 1.97–1.85, m (1H); 1.72, m (2H); 1.46, m (2H).

$^{13}$C NMR (CDCl$_3$,ref. 77.00): δ173.50, 130.42, 128.63, 80.23, 79.22, 61.74, 51.49, 48.95, 46.45, 33.86, 29.69, 29.31, 25.94, 22.92.

D. N-(4-Cyclohexylbutyl) 1H-imidazol-4-carboxamide

A suspension of 0.30 g of Part A acid (2.68 mmol) in 3.0 mL of dimethylformamide (DMF) (room temperature, argon) was treated with 0.52 g (3.21 mmol) of 1,1'-carbonyldiimidazole. Stirring was continued overnight. Triethylamine (0.45 mL, 3.21 mmol) was added followed by Part B amine (0.62 g, 3.21 mmol). Stirring was continued for 6 hours. The DMF was removed in vacuo (vacuum pump, dry ice-cooled receiver flask). Ethyl acetate and 30 mL of 0.1M HCl were added. The ethyl acetate layer was washed with 0.1M HCl (3 times, 5 mL each), saturated aqueous $K_2CO_3$ solution (3 times, 5 mL each), brine, dried over $Na_2SO_4$ and concentrated to yield 0.67 g of a yellow solid. Trituration from 10 mL of hexanes (1 crop) yielded 0.63 g of title compound in the form of an off-white solid.

E. [1S-[1α, 2α(Z),3α, 4α]]-6-[3-[[[(4-Methylphenyl)sulfonyl]oxy]methyl]-7-oxabicyclo[2.2.1]hept-2-yl]-4-hexenoic acid, methyl ester A solution of 4.00 g of Part C compound (15.73 mmol) in 200 mL of $CH_2Cl_2$ (room temperature, Ar) was treated with 19.08 mL of pyridine (235.95 mmol) then p-toluenesulfonyl chloride (5.97 g, 31.46 mmol). Stirring was continued for 3 days. TLC indicated the presence of unconsumed starting alcohol. An additional portion of p-toluenesulfonyl chloride was introduced (2.99 g, 15.73 mmol) and the reaction was continued overnight. Dichloromethane was removed under vacuum and replaced with 200 mL of diethyl ether. The cloudy ether solution was washed 5 times with 1M HCl (300 mL total), 1M NaOH solution (5 times, 250 mL total), brine, dried over $Na_2SO_4$ and evaporated in vacuo to yield an off-white sticky solid. Flash chromatography on 630 g of silica gel yielded 6.91 g of an off-white crystalline solid. The product was eluted with 60/40 hexanes/ethyl acetate after elution of p-toluenesulfonyl chloride with 85/15 hexanes/ethyl acetate. A minor contaminant was removed from the above product by a brief trituration with 25 mL of hexanes (0° C.) followed by filtration and 2 rinses with 10 mL each of hexanes (0° C.). Yield: 5.12 g of title compound as a white crystalline solid.

F. [1S-[1α, 2α(Z),3α, 4α]]-6-[3-[[4-[[(4-Cyclohexylbutyl)amino]carbonyl]-1H-imidazol-1-yl]methyl]-7-oxabicyclo[2.2.1]hept-2-yl]-4-hexenoic acid, methyl ester A solution of 0.31 g of Part D amide (1.23 mmol) in 2.0 mL of DMSO (room temperature, argon) was treated with 0.05 g of sodium hydride (1.23 mmol of a 60% mineral oil dispersion). Stirring was continued for 30 minutes. Part E compound was added (0.20 g, 0.49 mmol) and the reaction was run at 85° C. (oil bath temperature) for 2 hours. DMSO was removed in vacuo (vacuum pump, dry ice-cooled receiver flask). Ethyl acetate (30 mL) and 1M HCl were added. The ethyl acetate layer was washed 3 times with 1M HCl, 3 times with saturated aqueous $K_2CO_3$ solution, brine, dried over $Na_2SO_4$ and concentrated to yield 0.39 g of a viscous yellow oil. Flash chromatography on 27 g of silica gel (99.5/0.5 $CH_2Cl_2/CH_3OH$) yielded 0.16 g of title compound as a white crystalline solid. Also isolated was 0.16 g of unconsumed Part C compound.

EXAMPLE 10

[1S-[1α, 2α(Z), 3α, 4α]]-6-[3-[[4-[[(4-Cyclohexylbutyl)amino]carbonyl]-1H-imidazol-1-yl]methyl]-7oxabicyclo[2.2.1]hept-2-yl]-4-hexenoic acid A solution of 0.16 g of Example 9 ester (0.33 mmol) in 14.4 mL THF/2.9 mL $H_2O$ was treated with 3.29 mL of a 1M aqueous LiOH solution. The cloudy 2-phase reaction was stirred vigorously for 2 hours. The reaction mixture was cooled to 0° C. and brought to pH 1.0 with 6M HCl. THF was removed in vacuo and replaced with chloroform. The aqueous layer was extracted 4 times with chloroform, the combined chloroform layers (total 25 mL) were washed with brine, dried over $Na_2SO_4$ and concentrated to yield 0.14 g of a white taffy (90%). Concentration of the aqueous layer to c.a. 50% of its original volume was followed by 4 additional extractions with 8 mL each of chloroform. The combined chloroform layers were dried over $Na_2SO_4$, combined with the above 0.14 g of product, and evaporated in vacuo to yield 0.15 g of a white taffy (96%). This material was combined with 0.10 g of material from a previous batch and flash chromatographed on 18 g of silica gel. Elution with 99/1 ethyl acetate/PAW yielded a white solid which was dissolved in 4.0 mL of chloroform and filtered through a Gelman Acrodisc-CR disc (0.45 micron). Yield after chloroform removal: 0.14 g of a white solid; mp >50° C.

Anal. calc'd for $C_{27}H_{41}N_3O_4 \cdot 0.46H_2O$:

| | C, | 67.57; | H, | 8.80; | N, | 8.76 |
|---|---|---|---|---|---|---|
| Found: | C, | 67.77; | H, | 8.80; | N, | 8.56. |

EXAMPLE 11

[1S-(1α, 2α, 3α, 4α)]-2-[[3-[[4-[[(Cyclohexylbutyl)-amino]carbonyl]-1H-imidazol-1-yl]methyl]-7-oxabicyclo[2.2.1]hept-2-yl]methyl]benzenepropanoic acid, methyl ester

A. 3-(2-Bromophenyl)-2-propenoic acid, methyl ester

To a stirred suspension of 46.8 g (140 mmol, Aldrich) of methyl(triphenylphosphoranyl-idene)-acetate in 250 mL of dry tetrahydrofuran (THF) (distilled from potassium/benzophenone) at room temperature was added dropwise 25.0 g (135 mmol, Aldrich) of 2-bromobenzaldehyde, over 30 minutes. The reaction was mildly exothermic and became homogeneous. The resulting solution was stirred for 18 hours then concentrated in vacuo to give an oily solid. This material was slurried with 250 mL hexane and then filtered to remove solid triphenylphosphine oxide. The filtrate was concentrated in vacuo and the resulting oil was passed through a pad of silica gel (Merck silica, 9.5×2.0 cm, 1:4 ethyl acetate/petroleum ether elution). The eluant was concentrated in vacuo to give an oil. The crude oil was purified by bulb-to-bulb distillation (125–135°, ~0.5 mm) to afford 32.0 g (133 mmol, 98%) of title acrylate as a pale yellow liquid.

B. 2-Bromobenzenepropanoic acid, methyl ester

A mixture of 14.0 g (58.1 mmol) of Part A acrylate and 750 mg of 5% rhodium on alumina catalyst (MCB) in 150 mL of methanol (Burdick and Jackson) was stirred under an atmosphere of hydrogen (balloon) for 3 hours (until the starting material was consumed by TLC). The reaction mixture was passed through a 4 μM polycarbonate membrane and the filtrate was concentrated in vacuo to give an orange oil. The oil was dissolved in 100 mL of diethyl ether then washed with 50 mL of saturated sodium bicarbonate solution, 50 mL of brine, dried (magnesium sulfate) and concentrated in vacuo to afford 13.7 g (56.4 mmol, 97%) of title compound as a pale yellow liquid.

C. 2-Bromobenzenepropanol

To a solution of 13.6 g (56.0 mmol) of Part B compound in 75 mL of toluene (Burdick and Jackson, sieve-dried) cooled to −78° was added 118 mL (1.0 M in toluene, 118 mmol, Aldrich) of diisobutylaluminum hydride solution. The reaction was stirred at −78° for 2 hours then warmed to 0° for 2 hours. The resulting solution was quenched by very slow addition of 10 mL of 6 N HCl then more rapid addition of 100 mL of 6 N HCl. The reaction was stirred for an additional 10 minutes, then added to 50 mL of diethyl ether and the organic layer was separated. The organic layer was washed with two-100 mL portions of 1 N HCl, 100 mL of brine, dried (magnesium sulfate) and concentrated in vacuo to afford 12.0 g (55.8 mmol, 100%) of title compound as a colorless oil.

D. 1-Bromo-2-[3-[[Dimethyl(1,1,2-trimethylpropyl)silyl]oxy]propyl]benzene

To a solution of 29.0 g (135 mmol) of crude Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine then 200 mg (1.64 mmol, Aldrich) of 4-dimethylaminopyridine. The reaction mixture was stirred at room temperature for 18 hours. The resulting slurry was diluted with 100 mL of hexane, cooled to 0° with stirring for 15 minutes then filtered to remove solid triethylamine hydrochloride. The filtrate was concentrated in vacuo to give an oil. The crude oil was purified by flash chromatography (Merck silica, 15×10 cm, 1:9 ethyl acetate (EtOAc)/petroleum ether) to afford 45.5 g (127 mmol, 94%) of title compound as a colorless liquid.

E. [1S-(1α, 2α, 3α, 4α)]-[2-[3-[[Dimethyl-(1,1,2-trimethylpropyl)silyl]oxy]-propyl]-phenyl]-7-oxabicyclo[2.2.1]heptane-2,3-dimethanol To a solution of 5.00 g (14.0 mmol) of Part D compound in 30 mL of dry diethyl ether (distilled from ketyl) cooled to −100° was added dropwise 15 mL (1.7M in pentane, 25 mmol, Aldrich) of t-butyllithium solution over 15 minutes. The reaction mixture was stirred at −100° for 15 minutes then at 0° for 15 minutes. The resulting pale yellow anion solution was recooled to −78° then 30 mL of dry THF (distilled from ketyl) was introduced followed by the rapid addition of a solution of 875 mg (5.61 mmol) of [3aR-(3aα, 4β, 7β, 7aα)]-octahydro-4,7-epoxyisobenzolfurna-1-ol in 10 mL of THF. The reaction mixture was warmed to 0°, stirred for 1 hour, quenched with 5 mL of water then partitioned between 100 mL of water and 25 mL of ethyl acetate. The organic layer was separated and the aqueous layer was extracted with an additional 25 mL of ethyl acetate. The organic extracts were combined, dried (magnesium sulfate) and concentrated in vacuo to give an oil. The crude oil was purified by flash chromatography (Merck silica, 12×5.0 cm, 1:4 ethyl acetate/petroleum ether then 4:1 ethyl acetate/ petroleum ether) to afford 2.35 g (5.41 mmol, 97%) of title diasteromeric alcohols as a colorless oil.

F. [1S-(1α, 2α, 3α, 4α)]-2-[[2-[3-[[Dimethyl(1,1,2-trimethylpropyl)silyl]oxy]propyl]-phenyl]methyl]-7-oxabicyclo[2.2.1]heptane-3-methanol A mixture of 1.90 g (4.38 mmol) of Part E diastereomeric alcohols and 1.9 g of 20% palladium hydroxide on carbon catalyst (moist, <50% water, Aldrich) in 60 mL of glacial acetic acid was stirred rapidly under an atmosphere of hydrogen (balloon) for 5 hours. The reaction mixture was filtered through a 4μM polycarbonate membrane and the filtrate was concentrated in vacuo (room temperature bath). The residue was partitioned between 50 mL of water and 50 mL of ethyl acetate. The organic layer was separated, washed with 50 mL of 1M aqueous sodium hydroxide solution, dried (magnesium sulfate) and concentrated in vacuo to give an oil. The crude material was purified by flash chromatography (Merck silica, 12×5.0 cm, 1:2 ethyl acetate/petroleum ether) to afford 1.03 g (2.39 mmol, 55%) of title compound as a colorless oil. In addition, 573 mg (1.37 mmol, 30%) of Part C starting material (as a single diastereomer) was recovered.

G. [1S-(1α, 2α, 3α, 4α)]-2-[[3-(Hydroxymethyl)-7-oxabicyclo[2.2.1]hept-2-yl]methyl]benzenepropanoic acid, methyl ester A solution of 1.00 g (2.39 mmol) of Part F compound and 50 mg (0.41 mmol, Aldrich) of 4-dimethylaminopyridine in 6 mL of 1:1 dry pyridine/acetic anhydride was stirred at room temperature for 2 hours. The reaction mixture was concentrated in vacuo and the residue partitioned between 25 mL of ethyl acetate and 20 mL 1M aqueous HCl solution. The organic layer was separated, washed with 20 mL of 1M aqueous NaOH then 20 mL of brine, dried (magnesium sulfate) and concentrated in vacuo to afford the crude acetate as an oil.

To a solution of the crude acetate in 15 mL of reagent acetone cooled to 0° was added rapidly 3.3 mL (2.6M in $Cr^{+6}$, for preparation see Fieser & Fieser, "Reagents for Organic Synthesis," Vol. 1, p. 142) of Jones reagent. The reaction mixture was stirred for 2 hours, quenched by addition of 1 mL of isopropanol and stirred for an additional 30 minutes. The resulting green slurry was filtered through a pad of Celite. The filtrate was concentrated in vacuo and the residue partitioned between 5 mL of diethyl ether and 25 mL of water. The organic layer was separated and concentrated in vacuo to give the crude acetate-acid as an oil.

A solution of the crude acetate-acid in 15 mL of 2:1 1M aqueous NaOH/THF was stirred at room temperature for 30 minutes. The reaction mixture was cooled in an ice-bath, quenched by addition of 15 mL of 1M aqueous HCl solution then extracted with two-25 mL portions of diethyl ether. The ether extracts were combined, washed with 25 mL of brine and concentrated in vacuo to give the crude alcohol-acid as an oil.

A solution of the crude alcohol-acid in 10 mL of acidic methanol (prepared by addition of 0.5 mL of acetyl chloride to 10 mL of dry methanol at 0°) was stirred at 0° for 2 hours then concentrated in vacuo. The resulting oil was purified by flash chromatography (Merck silica, 15×3.0 cm, ethyl acetate) to afford 526 mg (1.76 mmol, 74% from Part F compound) of title compound as a colorless oil.

In Parts H, I and J that follow, all chromatographies were performed with E. Merck Kieselgel 60 silica gel (240-400 mesh).

H. [1S-(1α, 2α, 3α, 4α)]-2-[[3-[[[(4-Methylphenyl)sulfonyl]oxy]methyl]-7-oxabicyclo-[2.2.1]hept-2-yl]methyl]benzenepropanoic acid, methyl ester A solution of 0.33 g of Part G compound (1.08 mmol) in 14 mL of CH2Cl2 (room temperature, Ar) was treated with 0.41 g (2.15 mmol) of p-toluenesulfonyl chloride and pyridine (1.31 mL, 16.20 mmol). Stirring was continued overnight. TLC (silica, 50/50 hexanes/EtOAc) indicated unconsumed Part G compound. An additional portion of p-toluenesulfonyl chloride was introduced (0.21 g, 1.08 mmol) and the reaction was run over the weekend. TLC indicated complete consumption of Part G compound. Dichloromethane was evaporated in vacuo and replaced with 15 mL of EtOAc. The EtOAc solution was washed 3 times with 5 mL each of 1M HCl, 4 times with 3 mL each of saturated aqueous $K_2CO_3$ solution, brine, dried over $Na_2SO_4$ and concentrated to an oil. Flash chromatography on 38 g of silica gel yielded 0.42 g of title compound in the form of a colorless viscous oil (84%). The product was eluted with 50/50 hexanes/EtOAc after complete elution of unreacted p-toluenesulfonyl chloride with 80/20 hexanes/ EtOAc.

$^1$H NMR (270 MHz): δ7.78, d (2H) and 7.34, d (2H), J=8.21 Hz; 7.16–7.08, m (4H); 4.36, d (1H) and 4.16, d (1H), J=4.69 Hz; 4.13–4.01, m (2H); 3.68, s (3H); 2.91, t (2H); 2.63–2.57, m (3H); 2.45, s (3H); 2.40–2.16, m (3H); 1.76–1.54, m (2H); 1.50–1.43, m (1H); 1.35–1.27, m (1H).

$^{13}$C NMR (270 MHz): 173.04, 144.82, 138.48, 138.25, 132.95, 129.87, 129.47, 129.47, 128.92, 127.83, 126.53, 79.33, 78.84, 69.63, 56.76, 46.59, 46.25, 34.87, 30.21, 29.23,

I. [1S-(1α, 2α, 3α, 4α)]-2-[[3-[[4-[[(Cyclohexylbutyl)amino]carbonyl]-1H-imidazol-1-yl]methyl]-7-oxabicyclo[2.2.1]hept-2-yl]methyl]benzenepropanoic acid, methyl ester A solution of 0.30 g of Example 9, Part D acid (1.20 mmol) in 3.0 mL of DMSO (room temperature, Ar) was treated with 0.048 g of NaH (1.20 mmol of a 60% mineral oil dispersion). Stirring was continued for 30 minutes. A solution of 0.35 g of Part H compound (0.76 mmol) in 4 mL of DMSO was added and the reaction was run @ 80° C. (oil bath temperature) overnight. DMSO was removed in vacuo (vacuum pump, dry ice-cooled receiver flask). EtOAc (6 mL) and 1M HCl were added, the EtOAc layer was washed 3 times with 1M HCl (12 mL total), 3 times with saturated aqueous $K_2CO_3$ solution dried over $Na_2SO_4$ and evaporated in vacuo to yield 0.45 g of a tan taffy (>100%). Mineral oil was removed with hexanes (−78° C., 4 times, decanted, total 20 mL) without loss of product in the hexane decants by TLC. Flash chromatography on 42 g of silica gel (99/1 CH2Cl2/CH3OH) yielded 0.27 g of title compound in the form of a colorless viscous oil.

$^1$H NMR (270 MHz): δ7.62, 2 (1H); 7.48, s (1H); 7.18, m (4H); 4.26, d (1H) and 4.18, d (1H), J~4.10 Hz; 4.01, m (2H); 3.67, s (3H); 3.39, q (2H); 2.98, t (2H); 2.75–2.58, m (4H); 2.39, m (2H); 1.66–1.17, m (19H); 0.94–0.78, br t (2H).

$^{13}$C NMR (270 MHz): 172.72, 162.04, 138.16, 137.71, 136.48, 128.75, 128.67, 126.38, 120.89, 79.62, 78.37, 51.30, 47.71, 46.31, 46.12, 38.64, 37.19, 36.80, 24.51, 33.00, 30.00, 29.77, 29.29, 29.00, 27.20, 26.36, 26.03, 23.91.

EXAMPLE 12

[1S-(1α, 2α, 3α, 4α)]-2-[[3-[[4-[[(Cyclohexylbutyl)-amino]carbonyl]-1H-imidazol-1-yl]methyl]-7-oxabicyclo[2.2.1]hept-2-yl]methyl]benzenepropanoic acid A solution of Example 11 compound (0.27 g 0.50 mmol) in 11.8 mL THF.2.4 mL H2O was treated with 5.1 mL of a 1.0M aqueous LiOH solution. The cloudy, 2-layer reaction mixture was stirred vigorously for 4 hours. THF was removed in vacuo and the product was extracted 4 times with 5 mL each of chloroform. The combined chloroform layers were washed with brine, dried over $Na_2SO_4$ and concentrated to yield 0.24 g of a white solid. Flash chromatography on 17 g of silica gel with 99/1 EPAW* gave a residue which after EPAW removal in vacuo, was dissolved in a minimal amount of chloroform, filtered through a Gelman Acrodisc-CR filter disc (0.45 micron) and evaporated to yield a solid. Trituration from 4.0 mL of hexanes yielded 0.20 g of title compound in the form of an off-white solid.
*EPAW=EtOAc/PAW; PAW=20/6/11 Pyridine/HOAc/H2O ¹H NMR (270 MHz): δ7.70, s (1H); 7.54, s (1H); 7.44, br s (4H); 4.29, d, J=3.52Hz (1H); 4.18, d, J=4.10 Hz (1H); 4.02–3.98, m (2H); 3.38, q (2H); 3.00, t (2H); 2.74–261, m (4H); 2.41–2.36, m (2H); 1.69–1 50, m (9H); 1.40–1.17, m (10H); 0.88–0.83, m (2H).

¹³C NMR (270 MHZ): δ175.95, 162.44, 138,80, 138.02, 137.36, 137.04, 129.24, 126.85, 126.73, 126.16, 80.08, 78.79, 48.03, 46.88, 46.54, 39.28, 37.58, 37.15, 35.31, 33.38, 30.61, 29.92, 29.63, 29.09, 27.79, 26.72, 26.41, 24.28.

EXAMPLE 13

[1S-(1α, 2α, 3α, 4α)]-2-[[3-[[4-(4-Cyclohexyl-1-oxobutyl)-1H-imidazol-1-yl]methyl]-7-oxabicyclo[2.2.1]-hept-2-yl]methyl]benzenepropanoic acid, methyl ester

A. [1S-[1α, 2α, 3α, 4α]]-2-[[3-[[[(4-Methylphenyl)sulfinyl]oxy]methyl]-7-oxabicyclo-[2.2.1]hept-2-yl]methyl]benzenepropanoic acid, methyl ester A solution of 0.33 g of Example 11, Part G alcohol (1.08 mmol) in 14 mL of CH2Cl2 (room temperature, argon) was treated with 0.41 g (2.15 mmol) of p-toluenesulfonyl chloride and pyridine (1.31 mL, 16.20 mmol). Stirring was continued overnight. TLC (silica, 50/50 hexanes/EtOAc) indicated unconsumed Example 11, Part G alcohol. An additional portion of p-toluenesulfonyl chloride was introduced (0.21 g, 1.08 mmol) and the reaction was run over the weekend. TLC indicated complete consumption of Example 11, Part G alcohol. Dichloromethane was evaporated in vacuo and replaced with 15 mL of EtOAc. The EtOAc solution was washed 3 times with 5 mL each of 1M HC1, 4 times with 3 mL each of saturated aqueous K2CO3 solution, brine, dried over Na2SO4 and concentrated to an oil. Flash chromatography on 38 g of silica gel yielded 0.42 g of title compound in the form of a colorless viscous oil (84%). The product was eluted with 50/50 hexanes/EtOAc after complete elution of unreacted p-toluenesulfonyl chloride with 80/20 hexanes-/EtOAc.

B. 4-(4-Cyclohexyl-1-oxobutyl)-1H-imidazole

A suspension of 2.5 g of Example 1, Part D alcohol (11.24 mmol) in 55 mL of dioxane with 2.93 g, 33.77 mmol of MnO2 was refluxed under Ar overnight. TLC (silica 90/10 CH2Cl2/CH3OH) indicated the presence of unconsumed Example 1, Part D compound. An additional portion of MnO2 was introduced (1.47 g) and reflux was continued for 5 hours. TLC indicated complete consumption of Example 1, Part D compound. The reaction suspension was filtered through a pad of Celite and rinsed several times with a total of 100 mL of refluxing dioxane. Dioxane was removed in vacuo, the yellow oily residue was dissolved in 40 mL of ethyl acetate, washed 3 times with aqueous 2M trisodium citrate solution (20 mL total), dried over Na2SO4 and concentrated to yield 2.24 g of a light red-brown viscous oil (90%), of good purity by TLC. ¹H NMR and ¹³C NMR spectra of an earlier batch (J838-010-33) also indicated good crude product purity. Flash chromatography on 157 g of silica gel (97/3 CH2Cl2/CH3OH then 97/3 CH2Cl2/CH3OH) yielded 1.25 g of title compound in the form of an off-white solid (50%). The chromatography made little difference in product purity but greatly decreased the yield.

¹H NMR: δ7.80, br s (1H); 7.75, s (1H); 2.82, br s (2H); 1.85–1.45, m (9H); 1.35–1.05 (6H); 1.90–1.80, m (2H).

¹³C NMR: δ 138.54, 39.42, 37.52, 37.12, 33.29, 26.67 26.35, 22.17.

C.

[[1S-[(1o,2o,3o,4o)]-2-[[3-[[4-(4-Cyclohexyl-1-oxobutyl)-1H-imidazol-1-yl]methyl]-7-oxabicyclo[2.2.1]hept-2-yl]methyl]benzenepropanoic acid, methyl ester and

D. [1S-(1α, 2α, 3α, 4α)]-2-[[3-[[5-(4-Cyclohexyl-1-oxobutyl)-1H-imidazol-1-yl]methyl]-7-oxabicyclo[2.2.1]hept-2-yl]methyl]benzenepropanoic acid, methyl ester A solution of 0.48 g of Part B compound (2.2 mmol) in 3.0 mL of DMSO (Ar) was cooled to 0° C. To the solidified mass was added NaH dispersion. Stirring at 0° C. was continued for 20 minutes. Part A compound was added (0.40 g, 0.87 mmol) and the reaction was carried out at 72° C. (oil bath temperature) overnight. DMSO was removed with a vacuum pump/dry ice-cooled receiver flask. Ethyl acetate and 1M HC1 were added, the ethyl acetate layer was washed 3 times with 1M HC1 , 3 times with saturated aqueous K2CO3 solution, brine, dried over Na2SO4 and concentrated to yield 0.76 g of a viscous brown oil. Flash chromatography on 52 g of silica gel with 99/1 CH2Cl2/CH3OH yielded 0.36 g of a viscous yellow oil consisting of unseparated Part C and D compound. The product was re-chromatographed on 25 g of silica gel with 99/1 EPAW*. Yield: 0.26 g of Part C compound, a viscous yellow oil, 0.04 g of Part D compound and 0.08 g of a mixture of C and D compound.

Compound C

¹H NMR: δ 7.65, s (1H); 7.57, S (1H); 7.19, br s (4H); 4.28, d, J=3.69 Hz (1H); 4.19, d, J=4.22 H (1H); 4.03–4.00, m (2H); 3.68, s (3H); 2.97, m (4H); 2.78–2.56, m (4H); 2.39, m (2H); 1.73–1.69, m (9H); 1.42–1.39, m (2H); 1.26–1.18, m (8H); 0.08, m (2H).

Compound D

¹H NMR: δ 7.84, s (1H), 7.71, s (1H); 7.24–7.15 m (4H); 4.63, dd, J=12.66 Hz, J=3.70 Hz (1H); 4.23, d, J=4.22 Hz (1H); 4.17, d, J=4.22 Hz (1H); 4.05, dd, J=12.66 Hz, J=11.08 Hz (1H); 3.68 s (3H); 3.04, t (2H); 2.80, dd (partially obscured), J=4.22 Hz (1H); 2.78, t (2H); 2.67–2.63, m (3H); 2.44–2.37, m (2H); 1.73–1.63, m (9H); 1.39–1.10, m (11H); 0.95–0.80, m (2H).

EXAMPLE 14

[1S-(1α, 2α, 3α, 4α)]-2-[[3-[[4-(4-Cyclohexyl-1-oxobutyl)-1H-imidazol-1-yl]methyl]-7-oxabicyclo[2.2.1]-hept-2-yl]methyl]benzenepropanoic acid A solution of 0.26 g of Example 13 compound (0.52 mmol) in 12 mL of THF (room temperature, Ar) was treated with 5.0 mL of 1.0M aqueous LiOH solution. Rapid stirring of the 2-phase reaction mixture was carried out for 3.5 hours. THF was removed in vacuo. Chloroform and 1M HC1 were added (to pH 1.0), the aqueous layer was extracted 4 times with chloroform, the combined chloroform layers were washed with brine, dried over Na2SO4 and concentrated to yield 0.26 g of a solid. Flash chromatography on 17 g of silica gel with 99/1 EPAW* yielded 0.21 g of title compound in the form of a white solid.

*EPAW=EtOAc/PAW PAW=20/6/11 pyridine/acetic acid/H2O.

$^1$H NMR: δ 7.76, s (1H); 7.65, s (1H); 7.22–7.18, m (4H); 5.70–4.35, br s; 4.31, d (1H) and 4.21, d (1H), J=4.11 Hz; 4.11, dd, J=4.69 Hz, J=14.07 Hz (1H); 4.03, dd, J=13.00 Hz, J=14.07 Hz (1H); 2.99, t (2H); 2.90, t (2H); 2.74, dd, J=14.07 Hz, J=4.69 Hz (1H); 2.67–2.57, m (3H); 2.43–2.34, m (2H); 1.71–1.66, m (9H); 1.44–1.36, m (2H); 1.27–1.10, m (8H); 0.88–0.85, m (2H).

$^{13}$C NMR: δ 196.33, 176.21, 141.82, 138.68, 138.14, 137.91, 129.30, 129.06, 126.82, 126.65, 123.16, 79.79, 78.70, 48.06, 46.91, 46.53, 39.13, 37.46, 37.03, 35.04, 33.23, 30.61, 29.51, 29.03, 27.56, 26.64, 26.32, 21.48.

Examples of additional compounds in accordance with the present invention which may be prepared following the procedures outlined in the specification and working Examples include, but are not limited to the following.

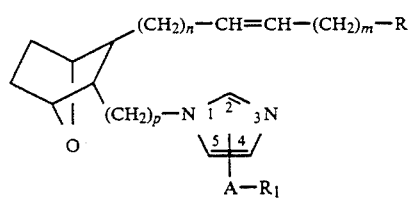

| Example No. | $(CH_2)_m$ m | $(CH_2)_n$ n | $(CH_2)_p$ p | A(position) | $R^1$ | R |
|---|---|---|---|---|---|---|
| 15 | 1 | 2 | 1 | CHOH-(2) | —C$_6$H$_{13}$ | CO$_2$H |
| 16 | 2 | 2 | 2 | C=O(4) | —(CH$_2$)$_4$—⟨S⟩ | CO$_2$H |
| 17 | 3 | 1 | 1 | CHOH(5) | ⟨S⟩ | CONHSO$_2$CH$_3$ |
| 18 | 1 | 2 | 1 | C=O(4) | —C$_2$H$_4$—⟨C$_6$H$_4$⟩—Cl | —CH$_2$-5-tetrazolyl |
| 19 | 2 | 3 | 1 | C(O)NCH$_3$(2) | C$_6$H$_5$ | CO$_2$H |
| 20 | 1 | 2 | 2 | -(4) | —CH$_2$C$_6$H$_5$ | —CH$_2$-5-tetrazolyl |
| 21 | 1 | 2 | 3 | -(4) | i-C$_3$H$_7$ | CONHSO$_2$C$_6$H$_5$ |
| 22 | 1 | 3 | 1 | -(4) | —CH$_2$—⟨S⟩ | CONHSO$_2$CH$_2$C$_6$H$_5$ |
| 23 | 1 | 2 | 1 | CHOH(5) | —(CH$_2$)$_3$—▷ | CO$_2$H |
| 24 | 2 | 2 | 3 | C=O(4) | □ | CO$_2$CH$_3$ |
| 25 | 1 | 2 | 2 | C=O(4) | CH$_3$ | CO$_2$Li |
| 26 | 1 | 3 | 1 | CHOH(5) | —⟨C$_6$H$_4$⟩—Cl | CO$_2$C$_2$H$_5$ |
| 27 | 1 | 2 | 2 | -(2) | (CH$_2$)$_2$C$_6$H$_5$ | CO$_2$H |
| 28 | 1 | 3 | 3 | — | H | —CH$_2$-5-tetrazolyl |
| 29 | 1 | 2 | 1 | C(O)NC$_2$H$_5$(5) | n-C$_5$H$_{11}$ | CO$_2$H |

-continued

| 30 | 2 | 3 | 1 | C(O)NH(4) | [thiane ring] | —CH$_2$-5-tetrazolyl |
| --- | --- | --- | --- | --- | --- | --- |
| 31 | 1 | 2 | 1 | — | H | CONHSO$_2$CH$_3$ |

[Structure: norbornane core with (CH$_2$)$_n$-phenyl-Y-(CH$_2$)$_m$-R substituent and (CH$_2$)$_p$-N(1)-(2)N(3) piperazine-like ring with positions 4,5 and A-R$_1$; with O on the ring]

| Example No. | (CH$_2$)$_m$ m | (CH$_2$)$_n$ n | (CH$_2$)$_p$ p | Y(position) | A(position) | R$^1$ | R |
| --- | --- | --- | --- | --- | --- | --- | --- |
| 32 | 1 | 2 | 1 | -(2) | CHOH-(2) | -n-C$_6$H$_{13}$ | CO$_2$H |
| 33 | 2 | 2 | 2 | O(2) | C=O(4) | —(CH$_2$)$_4$-[thiane] | CO$_2$H |
| 34 | 2 | 1 | 1 | -(3) | CHOH(5) | [thiolane] | CONHSO$_2$CH$_3$ |
| 35 | 1 | 2 | 1 | O(4) | C=O(4) | —(CH$_2$)$_2$-C$_6$H$_4$-Cl | —CH$_2$-5-tetrazolyl |
| 36 | 2 | 3 | 1 | -(2) | C(O)NCH$_3$(2) | —C$_6$H$_5$ | CO$_2$H |
| 37 | 1 | 2 | 2 | O(4) | -(4) | —CH$_2$C$_6$H$_5$ | —CH$_2$-5-tetrazolyl |
| 38 | 1 | 2 | 3 | -(2) | -(4) | i-C$_3$H$_7$ | CONHSO$_2$C$_6$H$_5$ |
| 39 | 1 | 3 | 1 | -(2) | -(4) | —CH$_2$-[thiane] | CONHSO$_2$CH$_2$C$_6$H$_5$ |
| 40 | 1 | 2 | 2 | -(3) | CHOH(5) | —(CH$_2$)$_3$-[cyclopropyl] | CO$_2$H |
| 41 | 2 | 2 | 3 | O(3) | C=O(4) | [cyclobutyl] | CO$_2$CH$_3$ |
| 42 | 1 | 2 | 3 | -(3) | C=O(4) | C$_2$H$_5$ | CO$_2$Li |
| 43 | 1 | 3 | 2 | O(2) | CHOH(5) | —C$_6$H$_4$-Cl | CO$_2$C$_2$H$_5$ |
| 44 | 1 | 2 | 1 | -(2) | -(2) | (CH$_2$)$_2$C$_6$H$_5$ | CO$_2$H |
| 45 | 1 | 3 | 1 | -(4) | — | n-C$_3$H$_7$ | —CH$_2$-5-tetrazolyl |
| 46 | 1 | 2 | 1 | O(3) | C(O)NC$_2$H$_5$(5) | n-C$_5$H$_{11}$ | CO$_2$H |
| 47 | 2 | 3 | 2 | -(2) | C(O)NH(4) | [thiane] | CONHC$_6$H$_5$ |
| 48 | 1 | 2 | 2 | -(2) | — | H | CONH$_2$ |
| 49 | 2 | 0 | 1 | -(3) | CHOH-(2) | n-C$_4$H$_9$ | CO$_2$H |
| 50 | 1 | 0 | 1 | -(2) | C=O(4) | C$_6$H$_5$ | CONHCH$_3$ |

-continued

| | | | | | | | |
|---|---|---|---|---|---|---|---|
| 51 | 1 | 2 | 2 | O(2) | CHOH(5) | —(CH₂)₄—[cyclopentyl] | CO₂H |
| 52 | 2 | 2 | 2 | -(3) | C=O(4) | —(CH₂)₅—[phenyl] | CO₂H |
| 53 | 1 | 1 | 1 | O(2) | C(O)NCH₃(2) | —(CH₂)₆—[cyclopentyl] | CONHCH₂C₆H₅ |
| 54 | 1 | 2 | 1 | -(2) | -(4) | —(CH₂)₄—[cyclohexyl] | CO₂H |

What is claimed is:

1. A compound having the formula

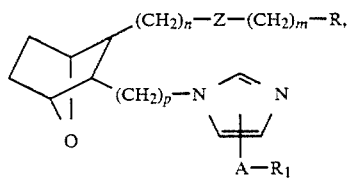

including all stereoisomers thereof, wherein
m is 0, 1, 2, 3 or 4;
n is 1, 2 or 3; p is 1, 2 or 3;
Z is —CH=CH—, —CH₂CH₂—or

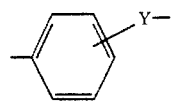

wherein Y is O or a single bond; with the provisos that when Z is

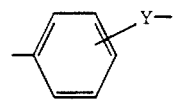

and m is 0, then Y is a single bone; and when Z is —CH=CH—or —CH₂CH₂—, m is 1, 2, 3 or 4;
R is CO₂H, CO₂alkali metal, CO₂lower alkyl, CONHSO₂R₂ (wherein R₂ is lower alkyl or aryl) or —CH₂-5-tetrazolyl;
A is CHOH, C=O,

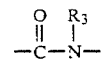

(wherein R₃ is H or lower alkyl), or a single bond;
R₁ is lower alkyl, phenyl, naphthyl C₃ to C₁₂ cycloalkyl or H, R₁ can be H only when A is a single bond.

2. The compound as defined in claim 1 having the formula

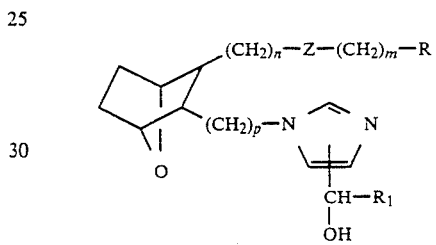

3. The compound as defined in claim 2 where m is 2, n is 1 and p is 1.

4. The compound as defined in claim 1 having the formula

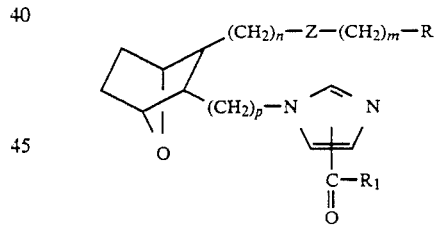

5. The compound as defined in claim 4 wherein m is 2, n is 1 and p is 1.

6. The compound as defined in claim 1 having the formula

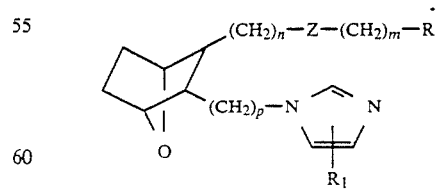

7. The compound as defined in claim 6 wherein n is 1, m is 2 and p is 1.

8. The compound as defined in claim 1 having the formula

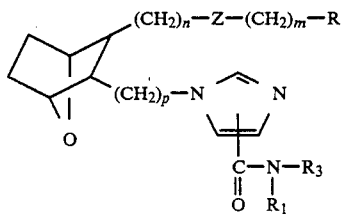

9. The compound as defined in claim 8 wherein n is 1, m is 2 and p is 1.

10. The compound as defined in claim 1 wherein R is $CO_2H$, $CONHSO_2R_2$ or $-CH_2$-5-tetrazolyl.

11. The compound as defined in claim 1 having the formula

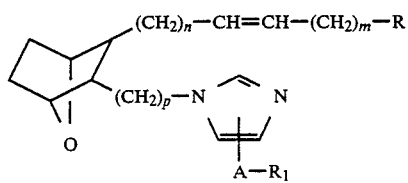

12. The compound as defined in claim 1 having the formula

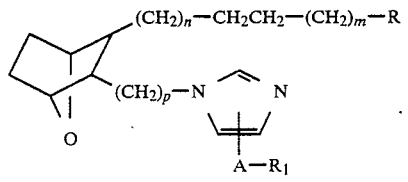

13. The compound as defined in claim 1 having the formula

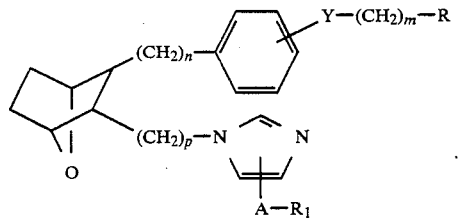

14. The compound as defined in claim 13 wherein Y is a single bond.

15. The compound as defined in claim 1 having the name [1S-[1α, 2α(Z), 3α, 4α]]-6-[3-[[4-(4-cyclohexyl-1-hydroxybutyl)-1H-imidazol-1-yl]methyl]-7-oxabicyclo[2.2.1]hept-2-yl]-4-hexenoic acid or its methyl ester.

16. The compound as defined in claim 1 having the name [1S-[1α, 2α(Z),3α, 4α]]-6-[3-[[4-(3-cyclohexylpropyl)-1H-imidazol-1-yl]methyl]-7-oxabicyclo[2.2.1]hept-2-yl]-4-hexenoic acid or its methyl ester.

17. The compound as defined in claim 1 having the name [1S-]1α, 2α(Z), 3α, 4α]]-6-[3-[[4-(4-cyclohexyl-1-oxobutyl)-1H-imidazol-1-yl]methyl]-7-oxabicyclo[2.2.1]hept-2-yl]-4-hexenoic acid or its methyl ester.

18. The compound as defined in claim 1 having then name [1S-[1α, 2α(Z), 3α, 4α]]-6-[3-[(1H-imidazol-1-yl)methyl]-7-oxabicyclo[2.2.1]hept-2-yl]-4-hexenoic acid or its methyl ester.

19. The compound as defined in claim 1 having the name [1S-[1α, 2α(Z), 3α, 4α]]-6-[3-[[4-[[(4-cyclohexylbutyl)amino]carbonyl]-1H-imidazol-1-yl]-methyl]-7-oxabicyclo[2.2.1]hept-2-yl]-4-hexenoic acid, or its methyl ester.

20. The compound as defined in claim 1 having the name [1S-(1α, 2α, 3α, 4α)]-2-[[3-[[4-[[(cyclohexylbutyl)amino]carbonyl]-1H-imidazol-1-yl]methyl]-7-oxabicyclo[2.2.1]hept-2-yl]methyl]benzenepropanoic acid or its methyl ester.

21. The compound as defined in claim 1 having the name [1S-(1α, 2α, 3α, 4α)]-2-[[3-[[4-(4-cyclohexyl-1-oxobutyl)-1H-imidazol-1-yl]methyl]-7-oxabicyclo[2.2.1]hept-2-yl]methyl]benzenepropanoic acid or its methyl ester.

22. A composition for inhibiting platelet aggregation and bronchoconstriction comprising an effective amount of a compound as defined in claim 1, and a pharmaceutically acceptable carrier therefor.

23. A method of inhibiting platelet aggregation which comprises administering to a mammalian host an effective amount of a compound as defined in claim 1.

24. A method of inhibiting bronchoconstriction associated with asthma, with comprises administering to a mammalian host an effective amount of a compound as defined in claim 1.

25. A method for improving post-ischemic myocardial dysfunction, which comprises administering to a mammalian host in need of such treatment an effective amount of a compound as defined in claim 1.

26. A method for treating toxemia during pregnancy, which comprises administering to a mammalian host in need of such treatment an effective amount of a compound as defined in claim 1.

27. A method for preventing or reducing venous thrombosis, which comprises administering to a mammalian host in need of such treatment an effective amount of a compound as defined in claim 1.

28. A method for preventing or educing platelet loss during extracorporeal circulation, which comprises administering to a mammalian host in need of such treatment an effective amount of a compound as defined in claim 1.

29. A method for treating burn injuries and/or promoting wound healing, which comprises administering to a mammalian host in need of such treatment an effective amount of a compound as defined in claim 1 in systemic or topical form.

30. A method for reducing post-ischemic myocardial injury, which comprises administering to a mammalian host in need of such treatment an effective amount of a compound as defined in claim 1 and an effective amount of a thrombolytic agent within 6 hours of a myocardial infarction.

31. The method as defined in claim 23 wherein said thrombolytic is t-PA, streptokinase, urokinase, prourokinase or anisoylated plasminogenstreptokinase activator complex.

* * * * *